United States Patent
Sumanaweera et al.

(10) Patent No.: US 9,320,916 B2
(45) Date of Patent: *Apr. 26, 2016

(54) HEART TREATMENT KIT, SYSTEM, AND METHOD FOR RADIOSURGICALLY ALLEVIATING ARRHYTHMIA

(75) Inventors: Thilaka Sumanaweera, San Jose, CA (US); Ed Gardner, San Jose, CA (US); Oliver Blanck, Bad Oldesloe (DE); Tao Cai, Sunnyvale, CA (US); Darrin Uecker, Sunnyvale, CA (US); Patrick Maguire, Menlo Park, CA (US)

(73) Assignee: CYBERHEART, INC., Mountain View, CA (US)

( * ) Notice: Subject to any disclaimer, the term of this patent is extended or adjusted under 35 U.S.C. 154(b) by 271 days.

This patent is subject to a terminal disclaimer.

(21) Appl. No.: 13/619,509

(22) Filed: Sep. 14, 2012

(65) Prior Publication Data
US 2013/0131425 A1 May 23, 2013

Related U.S. Application Data

(63) Continuation of application No. 12/838,113, filed on Jul. 16, 2010, now Pat. No. 8,784,290.

(60) Provisional application No. 61/271,177, filed on Jul. 17, 2009.

(51) Int. Cl.
*A61N 5/10* (2006.01)
*A61B 5/042* (2006.01)
(Continued)

(52) U.S. Cl.
CPC ............ *A61N 5/1037* (2013.01); *A61B 5/0422* (2013.01); *A61B 6/037* (2013.01);
(Continued)

(58) Field of Classification Search
CPC ............... A61N 5/00; A61N 5/10; A61B 6/00
See application file for complete search history.

(56) References Cited

U.S. PATENT DOCUMENTS

| 6,246,898 B1 | 6/2001 | Vesely et al. |
| 6,269,143 B1 | 7/2001 | Tachibana |

(Continued)

FOREIGN PATENT DOCUMENTS

| DE | 102005050000 A1 | 4/2006 |
| WO | 95/01757 A1 | 1/1995 |

(Continued)

OTHER PUBLICATIONS

International Preliminary Report on Patentability of PCT Application No. PCT/US2008/050656, mailed Jul. 23, 2009, 9 pages.

(Continued)

*Primary Examiner* — Christine H Matthews
(74) *Attorney, Agent, or Firm* — Kilpatrick Townsend and Stockton LLP

(57) ABSTRACT

Radiosurgical treatments of tissues of the heart mitigate arrhythmias and treat other tumerous and non-tumerous disease using an implanted fiducial positioned in or near the heart using cardiac catheterization techniques. The fiducials may be implanted after diagnostic and planning images of the target tissues have been acquired. Fiducial implantation may take place the day of a scheduled radiosurgical treatment. Techniques to accommodate post-planning fiducial implantation may include registration of the implanted fiducial location with the treatment plan, and active fiducials may limit collateral imaging radiation exposure while enhancing tracking accuracy.

23 Claims, 19 Drawing Sheets

(51) Int. Cl.
*A61B 5/00* (2006.01)
*A61B 6/03* (2006.01)
*A61B 6/00* (2006.01)
*A61B 8/08* (2006.01)
*A61B 19/00* (2006.01)

(52) U.S. Cl.
CPC ........... *A61N 5/1039* (2013.01); *A61N 5/1049* (2013.01); *A61N 5/1077* (2013.01); *A61B 5/7207* (2013.01); *A61B 5/7289* (2013.01); *A61B 6/03* (2013.01); *A61B 6/503* (2013.01); *A61B 6/504* (2013.01); *A61B 8/0883* (2013.01); *A61B 8/0891* (2013.01); *A61B 19/54* (2013.01); *A61B 2019/5251* (2013.01); *A61B 2019/5263* (2013.01); *A61N 5/1067* (2013.01); *A61N 2005/1061* (2013.01)

(56) References Cited

U.S. PATENT DOCUMENTS

| | | |
|---|---|---|
| 6,295,464 B1 | 9/2001 | Metaxas |
| 6,468,265 B1 | 10/2002 | Evans et al. |
| 6,487,438 B1 | 11/2002 | Widmark et al. |
| 6,488,629 B1 | 12/2002 | Saetre et al. |
| 6,690,965 B1 | 2/2004 | Riaziat et al. |
| 6,826,423 B1 * | 11/2004 | Hardy et al. ............... 600/429 |
| 6,889,695 B2 | 5/2005 | Pankratov et al. |
| 7,154,987 B2 | 12/2006 | Rubin et al. |
| 7,171,257 B2 | 1/2007 | Thomson |
| 7,229,417 B2 * | 6/2007 | Foerster et al. ............. 600/562 |
| 7,327,872 B2 | 2/2008 | Vaillant et al. |
| 7,429,910 B2 | 9/2008 | Domenz et al. |
| 8,784,290 B2 * | 7/2014 | Sumanaweera et al. ......... 600/1 |
| 2001/0011175 A1 | 8/2001 | Hunter et al. |
| 2002/0151794 A1 | 10/2002 | Li |
| 2003/0018251 A1 | 1/2003 | Solomon |
| 2003/0112922 A1 | 6/2003 | Burdette et al. |
| 2003/0220555 A1 | 11/2003 | Heigl et al. |
| 2004/0116810 A1 | 6/2004 | Olstad |
| 2004/0131150 A1 * | 7/2004 | Pankratov et al. ............... 378/65 |
| 2004/0267113 A1 | 12/2004 | Thomson |
| 2005/0038333 A1 | 2/2005 | Sra |
| 2005/0047544 A1 | 3/2005 | Fu et al. |
| 2005/0049478 A1 | 3/2005 | Kuduvalli et al. |
| 2005/0053267 A1 | 3/2005 | Mostafavi |
| 2005/0054916 A1 | 3/2005 | Mostafavi |
| 2005/0119560 A1 | 6/2005 | Mostafavi |
| 2005/0161051 A1 | 7/2005 | Pankratov et al. |
| 2005/0177044 A1 | 8/2005 | Rubin et al. |
| 2005/0182319 A1 | 8/2005 | Glossop |
| 2006/0002630 A1 | 1/2006 | Fu et al. |
| 2006/0004547 A1 | 1/2006 | Mostafavi |
| 2006/0072821 A1 | 4/2006 | Wang |
| 2006/0074292 A1 | 4/2006 | Thomson et al. |
| 2006/0178575 A1 | 8/2006 | Piacsek et al. |
| 2006/0241403 A1 | 10/2006 | Bruder |
| 2007/0053494 A1 | 3/2007 | Mostafavi |
| 2007/0058778 A1 | 3/2007 | Coleman et al. |
| 2007/0100224 A1 | 5/2007 | Bova et al. |
| 2007/0211849 A1 | 9/2007 | Movassaghi et al. |
| 2007/0219444 A1 | 9/2007 | Diaz et al. |
| 2007/0230765 A1 | 10/2007 | Wang et al. |
| 2008/0147111 A1 | 6/2008 | Johnson et al. |
| 2008/0177279 A1 | 7/2008 | Sumanaweera et al. |
| 2008/0177280 A1 | 7/2008 | Adler et al. |
| 2008/0292054 A1 | 11/2008 | Rosengren et al. |
| 2011/0166407 A1 | 7/2011 | Sumanaweera et al. |

FOREIGN PATENT DOCUMENTS

| | | |
|---|---|---|
| WO | 02/100485 A1 | 12/2002 |
| WO | 2004/033041 A1 | 4/2004 |
| WO | 2005/030330 A1 | 4/2005 |
| WO | 2005/087128 A1 | 9/2005 |

OTHER PUBLICATIONS

International Preliminary Report on Patentability of PCT Application No. PCT/US2008/050652, mailed Jul. 23, 2009, 11 pages.
International Search Report and Written Opinion of PCT Application No. PCT/US2010/042344, mailed Sep. 9, 2010, 21 pages.
U.S. Appl. No. 61/226,613, filed Jul. 17, 2009, filed name inventor: Thilaka Sumanaweera.
International Preliminary Report on Patentability of PCT Application No. PCT/US2010/042344, mailed Jan. 26, 2012, 20 pages.
International Search Report of PCT Application No. PCT/US2008/050652, mailed May 6, 2008, 6 pages.
International Search Report of PCT Application No. PCT/US2008/057133, mailed Sep. 17, 2008, 2 pages.
International Search Report of PCT Application No. PCT/US2008/050656, mailed Jun. 24, 2008, 5 pages.

* cited by examiner

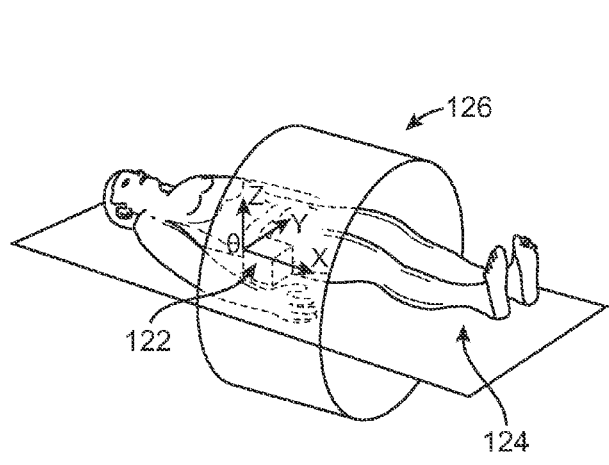
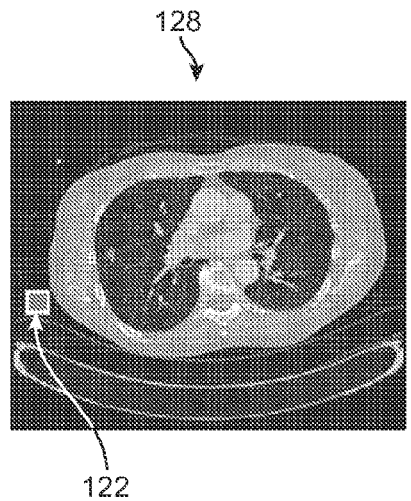
FIG. 9A  FIG. 9B
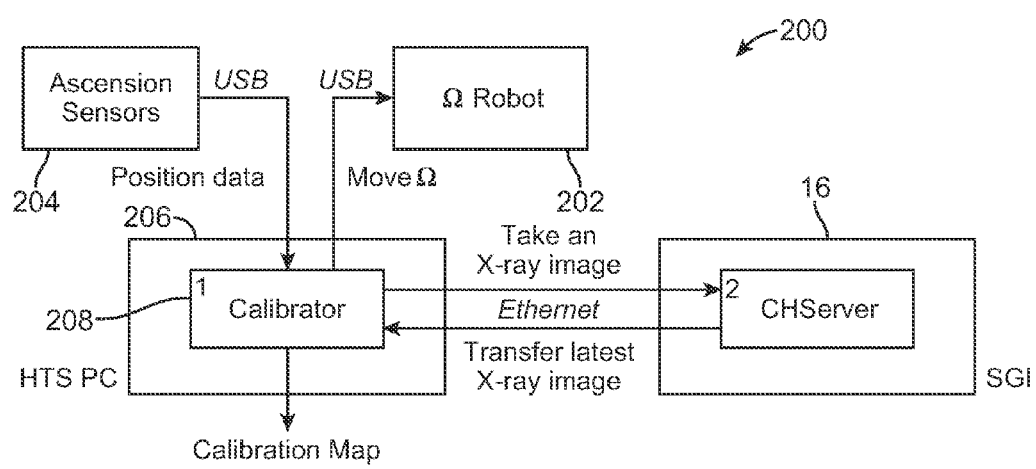
FIG. 9C

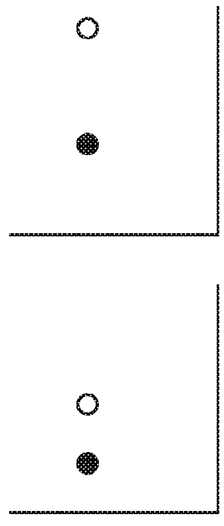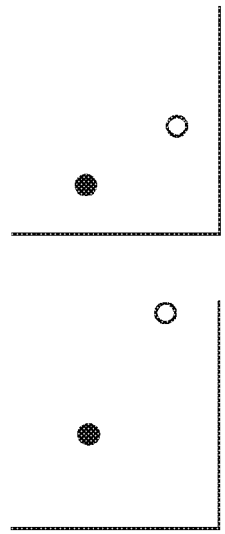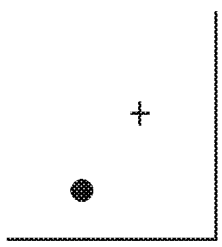

HEART TREATMENT KIT, SYSTEM, AND METHOD FOR RADIOSURGICALLY ALLEVIATING ARRHYTHMIA

CROSS REFERENCE TO RELATED APPLICATION DATA

This application is a Continuation of U.S. patent application Ser. No. 12/838,113 filed Jul. 16, 2010, which application claims the benefit under 35 USC 119(e) of U.S. Provisional Appln. No. 61/271,177 filed Jul. 17, 2009; the full disclosures, each of which are incorporated herein by reference in their entirety for all purposes.

BACKGROUND OF THE INVENTION

The present invention generally provides improved kits, systems, and methods for radiosurgical treatment of moving tissues in a patient body. Exemplary embodiments may deposit a sufficient radiation dose at a target region of a heart so as to treat an arrhythmia of the heart. Along with allowing treatment of tissues which move at a relatively rapid pace, embodiments of the invention may accommodate significant deformation or relative repositioning of regions of the heart without subjecting the patient to unnecessary long-term trauma or inconvenience, and without unnecessarily constraining the time available for radiosurgical treatment planning Tumors and other targets in the head, spine, abdomen, and lungs have been successfully treated using radiosurgery. During radiosurgery, a series of beams of ionizing radiation are often directed from outside a patient so as to converge at a target region, with the radiation beams often comprising MeV X-ray beams fired from different positions and orientations. The beams can be directed through intermediate tissue toward the target tissue so as to alter the biology of a tumor. The beam trajectories help limit the radiation exposure to the intermediate and other collateral tissues, while the cumulative radiation dose at the target can treat the tumor. The CyberKnife™ radiosurgical system (Accuray Inc.) and the Trilogy™ radiosurgical system (Varian Medical Systems) are two known radiosurgical treatment systems.

Modern radiosurgical systems incorporate imaging into the treatment system so as to verify the position of the target tissue and adjust to minor patient movements. Some systems also have an ability to treat tissues that move during respiration, and this has significantly broadened the number of patients that can benefit from radiosurgery. Radiosurgical treatments of other tissues that undergo physiological movements have also been proposed, including the directing of radiation toward selected areas of the heart for treatment of atrial fibrillation and other arrhythmias.

During atrial fibrillation, the atria lose their organized pumping action. In a healthy sinus rhythm, the atria contract, the valves open, and blood fills the ventricles or lower chambers. The ventricles then contract to complete an organized cycle of each heart beat. Atrial fibrillation, in contrast, has been characterized as a storm of electrical energy that travels across the atria causing the upper chambers of the heart to quiver or fibrillate. During atrial fibrillation, the blood is not able to empty sufficiently from the atria into the ventricles with each heartbeat. By directing ionizing radiation toward the heart based on appropriate lesion patterns, the resulting scar tissue may prevent recirculating electrical signals and thereby diminish or eliminate the atrial fibrillation.

While the proposed radiosurgical treatments of atrial fibrillation and other arrhythmias offer benefits by significantly reducing trauma for heart patients, improvements to existing radiosurgical treatment techniques may be helpful to fully realize the potential of such therapies. For example, tumors which move during respiration or the like may be targeted by surgically implanting high-contrast marker structures adjacent the targeted tumor. The marker acts as a fiducial, with the system identifying the location of the fiducial intermittently using biplane X-ray imaging techniques. Detailed images (such as computed tomography or CT) images of the heart tissues with the implanted fiducials are then obtained, and the series of intersecting radiation beams are carefully planned out so as to ablate the cancerous tumor. Unfortunately, taking enough X-ray images to adequately track the more rapid cardiac tissue movements associated with the heart beat cycle may subject collateral tissues to excessive quantities of image acquisition radiation. In fact, rather than tracking the implanted fiducials, known radiosurgical systems may monitor movement of a light-emitting diode (LED) fiducial array mounted on the skin of the patient so as to determine breathing and other patient movements. Biplane X-ray may then be acquired at a significantly slower rate than respiration: by only intermittently checking and revising the breathing cycle tracking with the X-ray images, such systems may adequately track respiration movement without imposing excessive imaging radiation. A variety of alternatives have been proposed for treatment of tissues which move with respiration and/or heartbeat, and while these proposals may eventually be shown to be viable for use in an arrhythmia treatment system, none has yet found widespread use. In the meantime, reliance on implanted fiducial structures in or near the tissues of the heart may present significant and unforseen challenges to general acceptance of radiosurgical treatments of tumerous and/or non-tumerous diseases of the heart.

In light of the above, it would be desirable to provide improved devices, systems, and methods for treating moving tissues of a patient, particularly by directing radiation from outside the patient and into the target tissues of a heart. It would be particularly beneficial if these improvements were compatible with (and could be implemented by modification of) existing radiosurgical systems, ideally without significantly increasing the exposure of patients to incidental imaging radiation, without increasing the system costs so much as to make these treatments unavailable to many patients, without unnecessarily degrading the accuracy of the treatments, and/or without causing unnecessary collateral damage to the healthy tissues of the patient despite the relatively rapid movement of the target tissues during beating of the heart.

BRIEF SUMMARY OF THE INVENTION

The present invention generally provides improved kits, systems, and methods for treating moving tissues of a patient. Embodiments of the invention allow improved radiosurgical treatments of tissues of the heart, often enhancing the capabilities of existing radiosurgical systems for targeting these relatively rapidly moving tissues so as to mitigate arrhythmias. Treatment of heart tissues may benefit from an implanted position surrogate for identification of the location of the target tissue, with the surrogate optionally comprising a fiducial marker positioned in or near the heart using cardiac catheterization techniques. Contrary to standard radiosurgical approaches, there may be significant benefits to positioning these fiducials after treatment planning images of the target tissues have been completed. Delaying the fiducial implantation until the day of a scheduled radiosurgical treatment may allow a precise beam plan to be developed for alleviating an arrhythmia while preserving collateral tissues, with the plan typically comprising both a relatively sophisticated lesion pattern in the heart and the associated series of radiation beams to induce that lesion. By avoiding the trauma to the heart of having temporary fiducials implanted for multiple days, the total trauma and inconvenience to the patient may be lessened, while allowing the fiducial markers to be safely positioned at desirable locations relative to the heart tissue structures so as to enhance targeting accuracy. Techniques to accommodate post-planning fiducial implantation may include registration of the implanted fiducial location with the treatment plan. Novel cardiac catheters and/or delivery structures having active fiducials may limit the need for X-rays (and thereby minimize collateral imaging radiation exposure). Enhanced planning and tracking techniques may also be employed, with the radiosurgical heart treatments described herein generally being compatible with many components of existing radiosurgical treatment systems. Hence, while the post-planning fiducial implantation treatments described herein may involve a number of significant changes from existing treatment approaches, these techniques may significantly expand the use of targeted radiation from outside a patient so as to treat conditions of the heart, without requiring huge investments and/or changes to existing radiosurgical treatment systems. Alternative embodiments may take advantages of many aspects described herein when planning images are obtained after implantation of surrogates with or without fiducials, and/or when planning takes place the same day as treatment.

In a first aspect, the invention provides a radiosurgical method for treating a patient having a body with a heart. The heart has a non-tumerous disease. The method comprises acquiring three-dimensional planning image data from the heart. An ionizing radiation treatment of a target region of the heart is planned using the three-dimensional planning image data so as to mitigate the disease. After the planning of the treatment, a position surrogate is implanted within the body. The target region of the heart is remodeled by directing the planned radiation from outside the body toward the target region with reference to the implanted surrogate.

In alternative embodiments, implanting of the surrogate may be performed prior to some or all of the acquisition of the planning image data and/or prior to some or all of the planning of the treatment. In some exemplary embodiments, the implanting of the surrogate, the treating of the target region, and the explanting of the surrogate from the body are performed on a treatment day. The acquiring of the planning image data of the heart and the planning of the treatment are performed on one or may dates prior to the treatment day. The planning image will typically be acquired more than one day prior to the treatment day, thereby allowing at least one day (and often more than one day, typically being at least three days, at least a week, or even more) for medical professionals and/or technical support personnel to plan the treatment so as to mitigate the patient's non-tumerous disease. When treating an arrhythmia, for example, an appropriate lesion pattern may be identified with the help of a heart specialist (such as a cardiologist, a heart surgeon, an electrophysiologist, and/or the like), who may work with a radiosurgical specialist (such as a radiologist, a radiation or medical physicist, and/or the like) so as to identify the target region in the heart suitable for alleviating the arrhythmia, the radiation dose gradients so as to avoid collateral damage to sensitive structures, and other details of the treatment plan. Other medical specialists may be consulted, optionally including an interventional cardiologist for identifying target regions of the heart for implanting of the surrogates, and the like. Hence, many of the treatment methods and systems described herein will benefit from a significant time between acquisition of the planning image and initiation of the radiation treatment. As it may be disadvantageous to leave image-able markers or other surrogates implanted in the heart for such an extended amount of time, and as the heart may shift significantly within the chest of the patient between acquisition of the planning image data and targeting of the selected region of the heart, post-planning implantation of the surrogates (along with accurate identification of the location of the target region relative to those surrogates) may enhance the benefits and effectiveness of the procedures. Typically, the planning of the treatment will comprise defining an estimated lesion of the heart based on the planned radiation, ideally allowing a graphical representation of the estimated lesion to be reviewed as part of the process.

In many embodiments, implanting of the surrogates will comprise advancing at least one elongate flexible body through a blood vessel. The surrogate may be coupled to tissue so that the surrogate exhibits heartbeat- and/or respiratory-induced movement. The implanted surrogate preferably comprises a non-colinear set of discrete fiducial markers so that a three-dimensional offset orientation between the surrogate and the target area can be determined from an image of the fiducial markers. In some embodiments, implanting of the surrogate may comprise screwing a helical structure of the elongate body into a soft, contractile tissue of the heart. Implanting of the surrogate may also include expanding an expandable body with a lumen or cavity bordered by the tissue, with the expandable body optionally comprising an inflatable balloon, a temporary stent-like structure, or the like, which can be safely and reversibly expanded within a coronary vessel or heart chamber of the beating heart so as to engage the surrounding tissue. In exemplary embodiments, implanting the surrogate may comprise fixing an active three-dimensional position indicator to the tissue, with the position indicator transmitting a position indicating signal that can be used to register a location of the implanted surrogate with the planning image data. Optionally, an image taken after implanting the surrogate may facilitate registration. For example, when the position indicating signal indicates an offset between the surrogate and a position sensor (or transmitter) disposed outside the body, the position indicating signal can be calibrated using post-implant image data that encompasses the heart and the position sensor. In one exemplary embodiment, the image data used for calibrating the position indicating signal comprises post-planning calibration image data, and a calibration position sensing signal is generated while a catheter tip engages a heart tissue. A positional relationship between the sensor and the body is maintained during acquisition of the calibration image data and the generation of the position sensing signal. More generally, the position indicator typically comprises a sensor or signal generator used within ultrasound or electromagnetic position indicating systems. The target region can be treated by directing the planned radiation using a position indicating signal from the position indicator between intermittent tracking verification images. Hence, position surrogates employing such active fiducial systems may limit the need for imaging X-rays (and thereby minimize collateral imaging radiation exposure).

The planning image data may be registered with the implanted surrogate by acquiring registration data between the implanting of the surrogate and the treating of the target region. The registration data often encompasses the heart and the implanted surrogate. The registration data typically comprises three-dimensional image data acquired using a first imaging modality. The planning image data may also be acquired with the same imaging modality. For example, the planning image data may comprise computed tomography (CT) data, and the registration image data may also comprise CT data, either acquired with the same CT system or a different CT system. Other imaging modalities that might be used for the registration and planning include magnetic resonance imaging (MRI), ultrasound (US), Positron Emission Tomography (PET), Single Positron Emmision Computed Tomography (SPECT), or the like. In other embodiments, the registration data may comprise three-dimensional image data acquired using a first imaging modality, while the planning image is acquired using a second imaging modality different than the first image modality. For example, US imaging may be used for registration while the planning is done using CT imaging.

In some embodiments, the registration data may comprise three-dimensional image data. A surface of the heart may be segmented in both the planning image data and the registration image data. Registering may then be performed using the segmented surfaces. Acquiring the image data and/or registration data with contrast agent disposed in the blood may facilitate identification of a blood/tissue interface surface bordering a chamber or vessel of the heart. An active position indicator of the surrogate may facilitate registration, with the surrogate again typically comprising a plurality of discrete image-able markers implanted so that the markers can define a three-dimensional offset orientation, typically with the markers being non-colinear. Registration may be facilitated by implanting fiducial markers having a high-contrast image at one or more associated heart tissue-defined locations, with the fiducial markers serving as the surrogate. For example, a catheter may implant a marker at or near the ostium of the coronary sinus, at or near an apex of the bifurcation between pulmonary blood vessels, or the like.

A variety of approaches may be used to align a radiation treatment source with the implanted fiducials. For example, alignment image data of the surrogate may be acquired, particularly where the target region is not easily visible. The surrogate images can then be brought into a desired position and orientation by movement of a patient support. Alternative alignment approaches may include providing appropriate offsets for a radiation source supporting robot or the like.

Preferably, a heartbeat cycle from the body will be monitored while acquiring the planning image. A time series of three-dimensional image datasets may be acquired, with the datasets distributed throughout the heartbeat cycle so as to indicate heart tissue movement with the heartbeat cycle. The planning of the treatment may include identifying radiation sensitive collateral tissues and determining a series of radiation beams suitable for providing a desired radiation dose in the target region without excessively irradiating the collateral tissue. The remodeling of the target region may be performed by monitoring the heartbeat cycle of the body, and tracking at least a portion of the movement of the tissue in response to the monitored heartbeat cycle and while directing the radiation to the target region. The tracking may use the time series of datasets.

The implanting of the surrogate will often comprise advancing at least one elongate flexible body through a blood vessel and coupling the surrogate to the heart so that the surrogate moves with the heartbeat cycle and respiratory cycle. A time average offset between the surrogate and the target region may be determined using the time series of image datasets. Tracking of the target region may be performed by determining a position of the surrogate, monitoring the heartbeat cycle of the body, and directing the radiation beam to the target region using the monitored heartbeat and respiratory cycles, the determined position of the surrogate, and the time average offset. Hence, deformation of the heart tissue between the surrogate and the target region need not necessarily be tracked by the system.

In exemplary embodiments, the time average offset may be determined for the heart cycle by identifying a series of three-dimensional offsets from the time series of image datasets. The time average offset may be applied throughout the heart cycle so that tissue deformation between the surrogate and the target region during the heartbeat cycle is untracked. The time average offset may be further determined by selecting an image dataset from among the time series of datasets. The selected dataset will preferably correspond to a calculated average of the measured series of offsets. The selected offset need not necessarily correspond to a quiescent phase of the heart cycle, nor to the calculated time average offset itself. In other embodiments, the calculated time average of the identified series of offsets may be used directly.

In another aspect, the invention provides a radiosurgical system for treating a patient body with a heart. The heart has a non-tumerous disease, and the system comprises an image capture device for acquiring three-dimensional planning image data from the heart. An implantable position surrogate is couple-able with a tissue of the heart within the body, optionally after the planning image is acquired. A radiation source is provided for transmitting a plurality of beams of ionizing radiation from outside the body. A processor system includes a planning module having an input for identifying a target region of the heart. The planning module generates a plan of the radiation beams in response to the target region and the planning image data. The processor system is coupled with the radiation source so as to direct the radiation beams toward the target region with reference to the implanted surrogate. The radiation beams thereby mitigate the disease by remodeling the target region of the heart.

In another aspect, the invention provides a treatment kit for use with a radiosurgical system to treat a patient body. The body has a heart with a non-tumerous disease. The radiosurgical system has a radiation source for transmitting a plurality of beams of ionizing radiation from outside the patient body per a plan so as to mitigate the disease. The radiosurgical system also has a plurality of tracking inputs for synchronizing the radiation beams with movement of a target region of the heart. The kit comprises an electrode couple-able to the patient so as to transmit a heart cycle signal of the patient to a first tracking input of the radiosurgical system. An elongate flexible body of the kit has a proximal end and a distal end insertable though a blood vessel of the patient. A position surrogate may be supported by the distal end of the flexible body so as to be insertable into operational engagement with the heart such that the surrogate moves with the heart suitably for generating a second tracking input of the radiosurgical system. Optionally, the distal end remains in operational engagement with the heart so that the distal end moves with the heart during treatment. Alternatively, the surrogate may be retrievable deployed from the distal end and the flexible body may be removed during application of the radiation beams.

The electrode, flexible body, and surrogate will typically be contained in a package, the package often being hermetically sealed and also containing instructions for use of the kit and the like. Additional components of the kit will also typically be included in the package.

The second input of the radiosurgical system may include a remote imaging system. The surrogate may comprise a set of passive, high-contrast fiducial markers having a sufficiently non-colinear configuration when deployed for defining a three-dimensional offset between the surrogate and the target region. The set of fiducials may have a substantially linear insertion configuration, and the surrogate may alternatively comprise an active ultrasound or electromagnetic component. The active surrogate may be included within an ultrasound or electromagnetic system that provides a signal to the second input so as to facilitate tracking of a position of the surrogate (and hence the target region). In many embodiments, a fixation surface may be provided for affixing the distal end of the elongate body to a tissue of the heart. The fixation surface may be defined by a radially expandable body, a vacuum seal body, or a helical fixation screw.

Many embodiments of the treatment kit may include a body surface marker affixable to an exposed surface of the patient body so as to facilitate imaging of a respiration movement of the body. For example, light emitting diodes (LEDs) may be mounted to a torso of the patient. The LEDs may be imaged by a standard video camera so as to monitor respiration using standard image processing techniques.

In many embodiments, the electrode may be included in a set of electrocardiogram (EKG) electrodes. An adhesive patch suitable for affixing an ultrasound imaging transducer to a skin of the patient may also be included with the kit. Components for accessing and implanting the surrogate may also be included. For example, an introducer sheath having a proximal end affixable to skin of the patient during the radiation treatments, a distal end insertable into the patient and a lumen therebetween may be provided. The lumen may sealingly receive the elongate body, typically with a valve member of the introducer sheath providing the sealing. Additional ports or channels can be provided so that multiple surrogate-supporting catheters can be positioned simultaneously. In exemplary embodiments, the kit may also include one or more additional components, such as a cardiac guidewire, imaging contrast deliverable through a lumen of the elongate body to a lumen or chamber of the heart, anesthetic skin cleansing solution, a locater needle, a guidewire, and/or the like.

In another aspect, the invention provides a radiosurgical system for treating a patient body with a heart, the heart having a non-tumerous disease. The system comprises an implantable position surrogate retrievably affixable to a tissue of the heart within the body from within a blood vessel. An image capture device is configured for acquiring three dimensional planning image data from the heart. A radiation source transmits a plurality of beams of ionizing radiation from outside the body, and a tracking system generates position data in response to a position of the surrogate. A processor system includes a planning module having an input for identifying a target region of the heart, the planning module generating a plan of the radiation beams in response to the target region and the planning image data. The processor system couples the tracking system with the radiation source so as to direct the radiation beams toward the target region with reference to the implanted surrogate such that the radiation beams mitigate the disease by remodeling the target region of the heart.

BRIEF DESCRIPTION OF THE DRAWINGS

FIGS. 9A and 9B schematically illustrate a system and method for registering a catheter tip with a CT dataset so as to calibrate a position sensing system including an active fiducial or the like;

FIG. 9C is a functional block diagram schematically illustrating an exemplary active catheter calibration module;

FIGS. 14a-14e schematically illustrate relative motion between a tracking surrogate and a target tissue as may be caused by tissue deformation, along with a calculated average target center;

DETAILED DESCRIPTION OF THE INVENTION

The present invention generally provides improved devices, systems, kits, and methods for treatment of tissue, often using radiosurgical systems. Embodiments of the invention may be particularly well suited for treatment of moving tissues, such as tissues of the heart (including adjacent vessels that move with the cardiac or heartbeat cycles). Such embodiments may take advantage of structures and methods which have been developed for treating tumors, particularly those which are associated with treatment of tissue structures that move with respiration cycles. The cardiac cycle is typically considerably faster than the respiration cycle, and overall treatment times can be fairly lengthy for effective radiosurgical procedures on the heart (typically being greater than 10 minutes, often being greater than one half hour, and in many cases being two hours or more). Hence, it will often be advantageous to avoid continuous imaging of the target and adjacent tissues using fluoroscopy or the like so as to limit exposure to excessive imaging radiation. Embodiments of the invention may also avoid any need for long-term implantation of fiducials in the moving tissues of the heart, thereby reducing the pain and discomfort to the patient, minimizing the risk of embolism, accumulation of thrombus, risk of infection, and the like. Advantageously, the invention can provide physicians and other medical professionals with adequate time for planning a proper radiosurgical course of treatment once a planning image dataset and other diagnostic measurements have been obtained.

Figure 1:
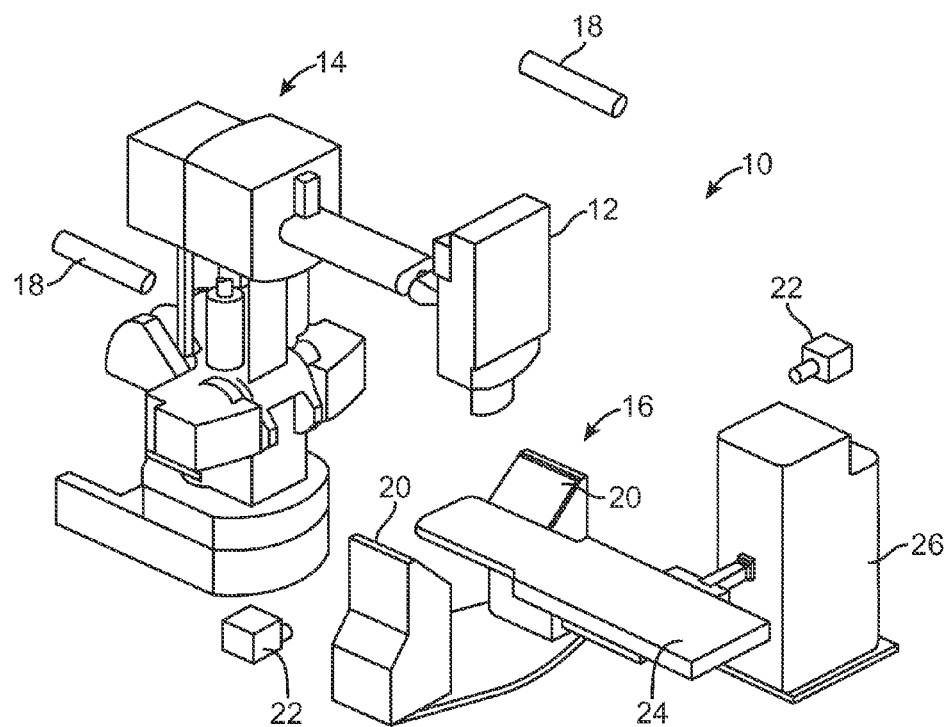
FIG. 1 is an exemplary CyberKnife™ stereotactic radiosurgery system for use in embodiments of the invention.

The present invention may take advantage of many components included in or derived from known radiation delivery systems. An exemplary modified CyberKnife™ stereotactic radiosurgery system 10 is illustrated in FIG. 1. Radiosurgery system 10 includes a lightweight linear accelerator 12 mounted to a robotic arm 14. An image guidance system 16 includes biplane diagnostic X-ray sources 18 and image detectors 20 so as to enhance registration between robot arm 14 and the target site. As the tissues in the target region may not present a high-contrast image, image guidance system 16 may use image processing techniques to identify the location of one or more surrogate structures, with the surrogates typically including a high-contrast natural tissue structure (such as a bone or the like) or an artificial implanted fiducial marker that moves in correlation with the target tissue. Target tracking may also make use of one or more surface image cameras 22, particularly for identifying movement of the chest wall corresponding to respiration. Cameras 22 may monitor light emitting diodes (LEDs) or other high-contrast fiducial markers visible on the patient's chest. A patient support 24 is movably supported by an alignment arm 26 so as to facilitate bringing the patient (and treatment site) into alignment with robot arm 14.

Figure 2:
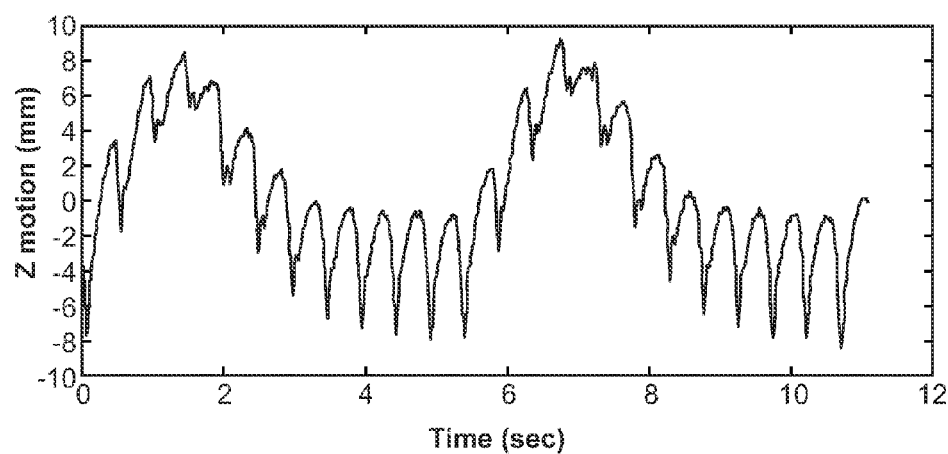
FIG. 2 is a graph showing exemplary data from the anterior/posterior motion of a point at the cavotricuspid isthmus inside the right atrium of a heart, showing movement associated with both the heart beat cycle and the respiration cycle.

FIG. 2 graphically shows the anterior/posterior motion of a point at the cavotricuspid isthmus inside the right atrium of a pig heart. As can be seen, the motion includes two components: a slowly varying breathing component and a more rapid cardiac component. Embodiments of the present invention may address either and/or both of these motion components. For example, robot arm 14 may move linear accelerator 12 synchronously with a target site so as to compensate both for the respiration component, and for the cardiac component of overall motion. Alternatively, synchronous movement of robot arm may track only the respiration component while disregarding the cardiac component in at least one or more degrees of freedom. In some embodiments, robot arm 14 may track the respiration component of motion with gating of linear accelerator 12 applied so as to limit the radiation beam to portions of the heartbeat cycle where the target tissues are sufficiently aligned with the robot so as to mitigate or eliminate cardiac motion-induced errors. As the significance of the different motion components in different degrees of freedom may vary, differing combinations of motion component tracking, motion component disregarding, and radiation gating may be employed. Exemplary tracking approaches are described in more detail in U.S. Patent Publication 2008/0177280 in the name of Adler et al., as published on Jul. 24, 2008 (the full disclosure of which is incorporated herein by reference.)

Figure 3:
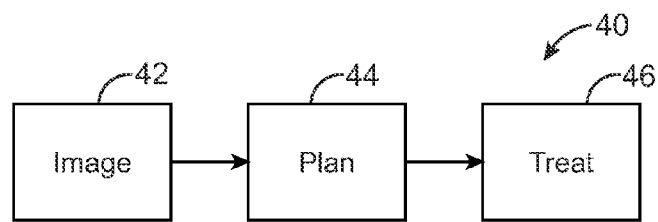
FIG. 3 schematically illustrates a method for treating a target tissue using a radiosurgical system.
Figure 4:
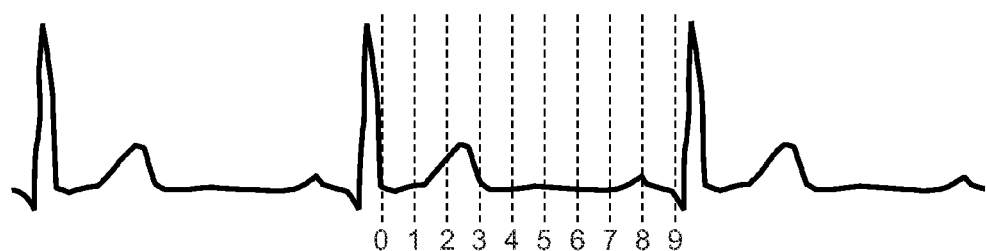
FIG. 4 is an illustration of an EKG waveform showing exemplary phases where a time sequence of CT volumes are acquired.

Referring now to FIG. 3, a relatively simple treatment flowchart 40 can represent steps used before and during radiosurgical treatment according to embodiments of the present invention. The internal tissues are imaged 42 for planning purposes, typically using a remote imaging modality such as a computed tomography (CT), magnetic resonance imaging (MRI), ultrasound imaging, X-ray imaging, PET, SPECT, optical coherence tomography, a combination of these, or other imaging modalities. Note that the tissue structure which will actually be targeted for radiation remodeling need not necessarily be visible in the image, so long as sufficiently contrasting surrogate structures are visible in the image data to identify the target tissue location. The planning imaging used in many embodiments will include a time sequence of three-dimensional tissue volumes, with the time sequence typically spanning one or more movement cycles (such as a cardiac or heartbeat cycle, a respiration or breathing cycle, and/or the like). In exemplary embodiments, the image data comprises a series of CT slices through the heart so as to provide volumetric or three-dimensional image data. The time series of three-dimensional heart images are preferably acquired at times that are distributed throughout the heartbeat cycle, so that the image planning data effectively comprises a time series of three-dimensional image datasets providing information regarding the motion of cardiac tissues during the heartbeat. FIG. 3 shows a typical heartbeat electrocardiogram (EKG) waveform from which ten phases have been identified and for which ten associated CT volumes are acquired. In some embodiments, the target tissue may be outlined in each of the ten volumes, or the target outline may be identified in one CT volume and automatically tracked over the other CT volumes. As will be described in more detail hereinbelow, other alternatives include selecting an appropriate one of the three-dimensional image datasets from the time series, generating an average positional dataset, or the like. Regardless, acquisition of the series of three-dimensional datasets can be performed using any of a variety of commercially available CT systems.

Referring still to FIG. 3, based on the imaging data obtained from image step 42, a plan 44 can be prepared for treatment of the tissue at the target site. The plan typically comprises a target region and a series of radiation beams which intersect within the target region. The radiation dose within the target tissue should be at least sufficient to provide the desired remodeling effect. Typically, the radiation dose will be sufficient to ablate tissue, inhibit contractile pathways within the heart, inhibit arrhythmogenesis, and/or the like. Radiation dosages outside the target tissue will preferably decrease with a relatively steep gradient so as to inhibit excessive damage to collateral tissues, with radiation dosages in specified sensitive and/or critical tissue structures often being maintained below a desired maximum threshold to avoid deleterious side effects.

Figure 5:
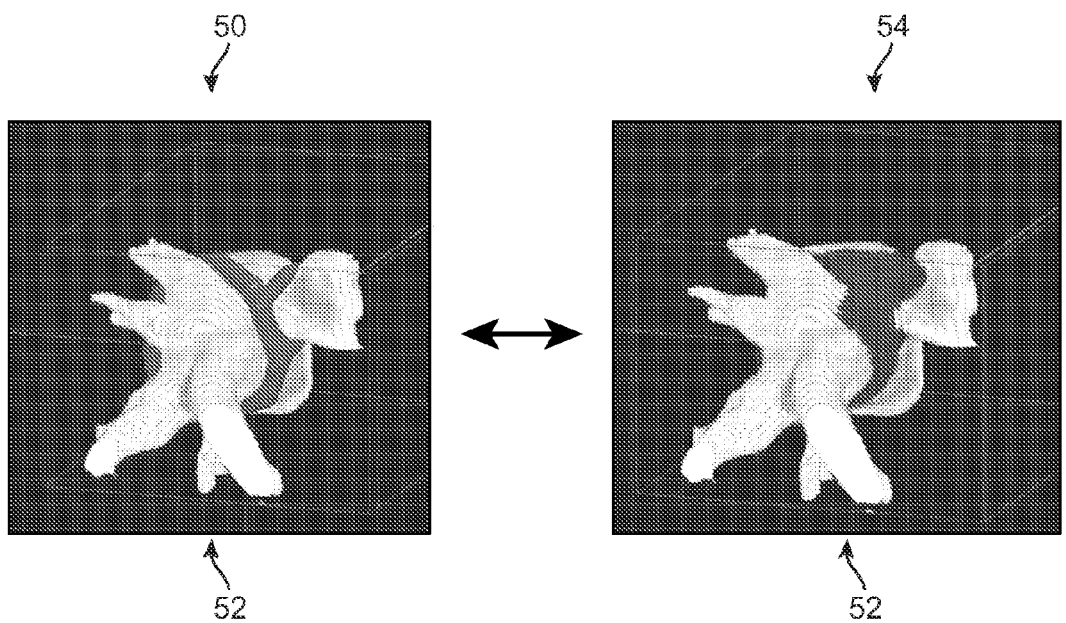
FIG. 5 graphically shows portions of a user interface display, including a planning input for a target region so as to treat an arrhythmia of a heart, along with a graphical representation of a lesion of the heart estimated by components of the treatment system.

Referring now to FIGS. 3 and 5, an exemplary treatment planning module and user interface allows the system user to input a desired lesion pattern with reference to a surface of a tissue. For treatment of moving tissues of the heart so as to inhibit arrhythmias, the reference heart surface may comprise the blood/tissue interface or the inner surface of one or more heart chambers and adjacent blood vessels. Alternative embodiments may employ an outer surface of the heart as the reference surface, although the surface may be more easily identified from the three-dimensional planning image data by introducing imaging contrast agent during the planning image acquisition step 42. The boundary between the blood (including the added contrast) and the heart tissue in each slice of the CT data can be segmented in one, some, or all of the volumetric datasets associated with the cardiac cycle phases. The segmented regions can be stacked or assembled together, and smoothing techniques can be applied between the boundaries of the slices. This allows the planning medical professionals to input an appropriate lesion pattern as a series of lines or curves relative to the heart tissue surface, with the lines being expanded to volumes so as to provide the desired therapeutic benefit. Alternatively, the lesion pattern may be defined by delineating a volume of tissue between segmented epicardial and endocardial surfaces of the heart chambers. In such embodiments, the user may optionally define the lesion with reference to the myocardial wall surface. Additional details regarding the input of a desired treatment region 50 relative to a heart surface 52 are provided in U.S. Patent Application No. 61/226,613, entitled, "Heart Tissue Surface Contour-Based Radiosurgical Treatment Planning" (Attorney Docket No. 021902-002100US), the full disclosure of which is incorporated herein by reference. Once the target region has been identified, existing radiosurgical planning approaches to identification of radiation sensitive structures may be implemented. Similarly, existing radiosurgical radiation beam calculating modules may be used to determine the resulting radiation distribution.

Along with inputting a desired lesion pattern (as schematically illustrated on the left side of FIG. 5), the planning module and user interface will preferably output an estimate of the actual radiation exposure along the surface of a heart, preferably in the form of an estimated heart surface lesion 54 (as schematically illustrated on the right side of FIG. 5). Estimated lesion 54 may represent the portion of heart tissue surface 52 which receives a radiation dose above a necrotic threshold, optionally based on radiation beams and radiation dose output from an existing radiosurgical treatment planner. Alternative patterns may represent an estimate of tissue which will receive a sufficient dose of radiation for therapeutic remodeling so as to inhibit the arrhythmia. The user may interactively develop the plan based on iterative input into and output from the planning treatment module. The exemplary display of estimated lesion 54 shown on heart tissue surface 52 seen in FIG. 5 shows a highlighted (false color) area of the left atrial endocardial surface that receives a radiation dose higher than a first (lower) threshold and less than a second (higher) threshold. Alternative displays may indicate a tissue surface area which receives a sufficient dose to eventually cause the tissue to scar, to necrose, to ablate, and/or the like, with the indicated tissue optionally being highlighted using a color or tissue surface image which corresponds to the eventual tissue state (for example, so that scar tissue that is typically whiter than a corresponding healthy tissue is indicated by a whiter shade than the surrounding tissue, or the like).

Figure 6B:
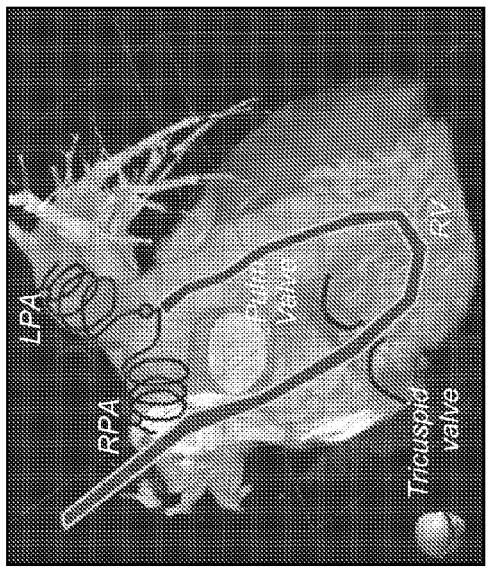
FIGS. 6A-6C show catheter-based fiducials deployed in lumens and/or chambers of the heart so as to provide a tracking surrogate.
Figure 6C:
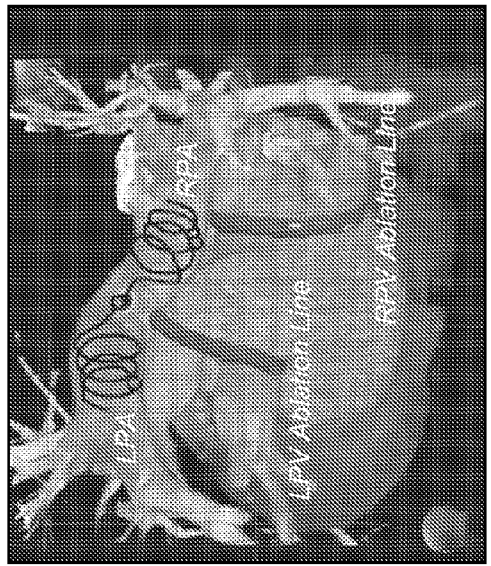
Figure 6A:
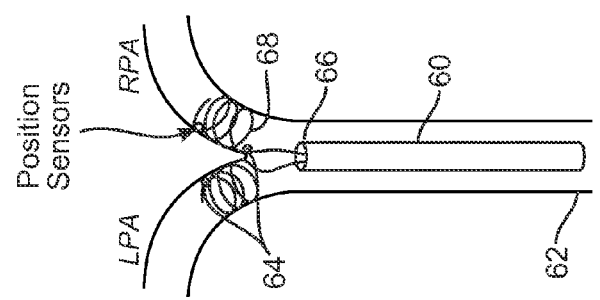

Referring once again to FIG. 3 (along with reference to FIGS. 1 and 6A-6C) after completion of plan 44, radiosurgical treatment of heart 46 may be initiated by positioning the patient on patient support 24, bringing the patient into alignment with robot arm 14, and directing the planned series of radiation beams from the linear accelerator 12 to the target region of the heart. However, as noted above, the target region of the heart may not be readily identified in the images obtained by image guidance system 16. To enhance tracking of the soft tissue of the heart, it will often be advantageous to advance a catheter 60 through a blood vessel 62 so as to couple one or more surrogate structures 64 to a tissue that moves in correlation with the target region of the heart. In the embodiment of FIGS. 6A-6C, catheter 60 has a distal end 66 with two stent-like structures 68. The stent-like structures 68 can be expanded atraumatically within a lumen of a blood vessel or chamber of the heart so as to support fiducials 64 against the tissue surface of the surrounding luminal or chamber wall. Stent-like structures 68 can also be radially contracted and withdrawn proximally after radiosurgical treatment of the target region. The exemplary method illustrated in FIGS. 6A-6C shows a series of fiducials 64 being deployed in a non-colinear configuration in the left pulmonary artery LPA, the right pulmonary artery RPA, and adjacent the isthmus or septum of the bifurcation between the left and right pulmonary arteries. Such a non-colinear configuration facilitates defining a three-dimensional offset based on image data of the fiducials, with the exemplary offset extending between the fiducials and the target region(s), the target regions here represented by the left pulmonary vein LPV ablation line and right pulmonary vein RPV ablation line, as seen in FIG. 6C.

Figure 7:
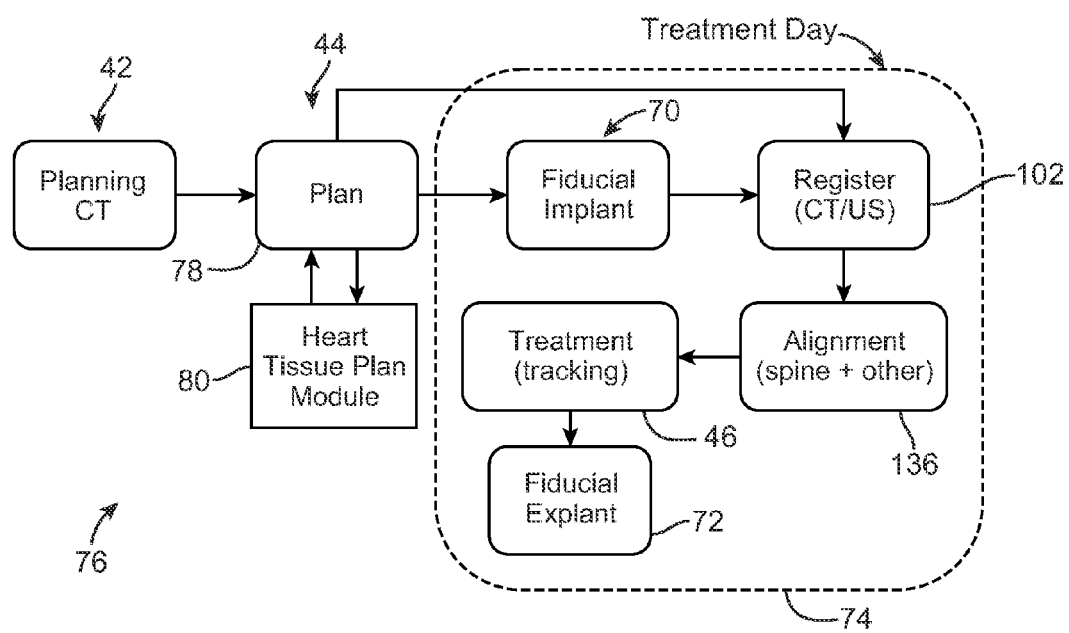
FIG. 7 schematically illustrates a radiosurgical system and method for treating a heart in which fiducials are implanted into the heart or adjacent structures after planning of the target regions and the associated series of radiation beams.

Referring now to FIGS. 3 and 7, the time associated with acquiring images 42 and planning treatments 44 may, taken together, represent at least a significant portion of a day. The radiosurgical treatments themselves 46 may likewise take a significant amount of time, while the surgical implantation and explantation of fiducials 70, 72 also involve some time. As it is generally desirable to avoid leaving structures implanted in or adjacent the heart tissues for more time than is necessary, it will often be beneficial to perform the fiducial implantation 70 and fiducial explantation 72 on a radiosurgical treatment day 74, while the imaging 42 and planning 44 are performed prior to the treatment day. However, a result of this post-planning implantation of fiducials 70 is that the fiducial images and locations may not be available in the planning image data prior to the treatment day. Note that, for this reason, post-planning fiducial implantation may be contrary to standard radiosurgical treatment practice.

In light of the above, an exemplary treatment methodology 76 generally includes obtaining a planning image in the form of CT data 42 without any artificial or implanted tracking fiducials. Contrast agent will typically be used during the image acquisition to facilitate identification of the blood-heart tissue surface, and the planning image data will preferably include a time series of three-dimensional datasets, with each three-dimensional dataset typically including a series of offset planar scans through the heart tissue.

As described above, planning may be performed using a general radiosurgical treatment plan module 78, along with a specialized heart treatment plan module 80. The general plan module 78 may be used during treatment of tumors, for example, to identify isocentric or other irradiation target profiles in some of the planar CT slices of the planning image. Radiation-sensitive collateral tissues may also be identified in the planar CT scans, and based on this input the general treatment planning module may generate a series of radiation beams and associate dose information in the planes of the CT scans. So as to facilitate treatment of non-tumerous diseases of the heart (such as arrhythmias) with tissue-surface based lesion patterns, heart tissue plan module 80 may interface with (and take advantage of) the capabilities of general plan module 78.

Heart tissue plan module 80, as with other data-processing modules described herein, will typically comprise computer processing hardware and/or software, with the software typically being in the form of tangible media embodying computer-readable instructions or code for implementing one, some, or all of the associated method steps described herein. Suitable tangible media may comprise a random access memory (RAM), a read-only memory (ROM), a volatile memory, a non-volatile memory, a flash memory, a magnetic recording media (such as a hard disk, a floppy disk, or the like), an optical recording media (such as a compact disk (CD), a digital video disk (DVD), a read-only compact disk, a memory stick, or the like). The various modules described herein may be implemented in a single processor board of a single general purpose computer, or any one or more of the modules may run on several different processor boards of multiple proprietary or commercially available computer structures, with the code, data, and signals being transmitted between the processor boards using a bus, a network (such as an Ethernet, an Intranet, or an Internet), via tangible recording media, using wireless telemetry, or the like. The code may be written as a monolithic software program, but will typically comprise a variety of separate subroutines and/or programs handling differing functions in any of a wide variety of software architectures, data processing arrangements, and the like. Nonetheless, breaking the functionality of the program or hardware into separate functional modules is useful for understanding the capabilities of the various aspects of the invention.

The exemplary heart tissue plan module 80 interfaces with the Multiplan™ planning module of the CyberKnife™ radiosurgical system. Rather than inputting shapes onto the planar CT scans, the user interface of the heart plan module 80 can define lines and/or curves on the tissue surface, with the heart tissue plan module identifying the associated shapes on the CT scan planes. The heart tissue plan module also graphically displays an estimated lesion of the heart tissue on a display of either heart plan module 80 or radiosurgical plan module 78 (as generally described above regarding FIG. 5.) This allows the medical professional or professionals planning the patient's treatment to verify that the lesion pattern is appropriate and capable of producing the desired therapeutic benefits. An exemplary heart tissue plan module 80 also simulates the effects of gross misalignment between the patient and/or heart and the radiosurgery treatment system 10 (with associated output to the planning medical professional(s)), and/or provides output to the planning medical professionals regarding tracking errors (ideally in 6 degrees of freedom) on the estimated lesion location and shape.

On a calendar day after plan 44 has been completed, and preferably on a treatment day 74, the patient will undergo surgical implantation of the tracking surrogate or fiducial 70. In some embodiments, the fiducial or fiducials may be implanted the day prior to treatment being initiated, and/or treatment may take place on more than one day (with fiducials optionally being explanted and new fiducials being implanted between treatments). Preferably, the fiducials are implanted by advancing a distal end of a catheter through a blood vessel to a tissue of the heart, with the distal end of the elongate flexible catheter body coupling a high-contrast fiducial set to the heart tissue so that the fiducial moves in correlation with the target tissue. Exemplary coupling mechanisms include radially expandable balloons or stent-like structures (optionally including helical coils, braids, or the like) as described above regarding FIGS. 6A-6C. These expandable bodies may be biased to expand radially when released from a surrounding catheter sheath (such as by pulling the sheath proximally from over the expandable body) or may be expanded by introducing a fluid (typically a liquid such as saline or a gas such as air) into an anterior of a balloon, shortening a length between a proximal end and a distal end of the expandable body, or the like. The expandable body will typically be configured to contract radially such as by advancing a sheath over the expandable body, emptying inflation fluid, pulling a filament of a helical coil into a sheath, or the like. A wide variety of alternative reversibly expandable structures are known in the stent field, and many of these can be modified for use to temporarily affix a surrogate to a tissue of the heart, either inside a chamber of the heart or within an adjacent blood vessel.

Figure 7A:
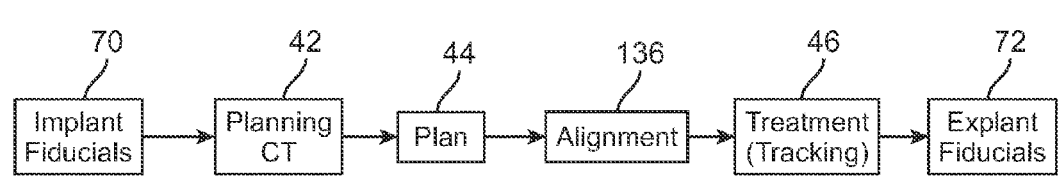
FIG. 7A schematically illustrates an alternative radiosurgical system and method for treating a heart in which fiducials are temporarily implanted into the heart or adjacent structures before planning of the target regions and the associated series of radiation beams, and are explanted after treatment.

FIG. 7A schematically illustrates an alternative workflow that may employ many aspects of the inventions described herein. In alternative treatment workflow 76', the fiducial implantation 70 may take place prior to acquiring a planning CT 42 or other planning image. Following acquisition of the planning image, the patient may return home for treatment on another day (so as to allow treatment planning 44 to take at least a significant portion of a day, the planning often taking one or more days to complete). Tethered intraluminal surrogate systems (in which fiducials remain tethered to an intraluminal access site by an elongate catheter body) might optionally be temporarily implanted for more than one day. Alternatively, it may be beneficial to instead employ non-tethered intraluminal surrogate systems (in which temporarily implanted and released fixation structures support the fiducials within a lumen or chamber of the heart, while no catheter body extends between the vascular access site and the surrogate system). Such a non-tethered fixation structures will preferably be configured to facilitate subsequent coupling of a catheter thereto and endoluminal recapture and retrieval of the surrogate system during fiducial explantation 72. Still further alternative embodiments of workflow 76' may employ an in-patient and/or same day treatment approach. For example, fidicial implantation 70, planning image acquisition 42, treatment planning 44, alignment of the patient with the treatment system 136, and treatment 46, and optionally even explanation 72 may be coordinated so as to be completed within one day, often with the patient remaining at the hospital or other treatment facility throughout the treatment period. Related alternative embodiments may extend beyond a single day to two or three days (though typically less than a week), with at least explantation 72 (and optionally the treatment itself) occtwo days, three days, or within one week), often while the patient remains at the hospital or other treatment site. Fiducial explantation 72 again typically occurs at the end of the procedure.

Figure 6E:
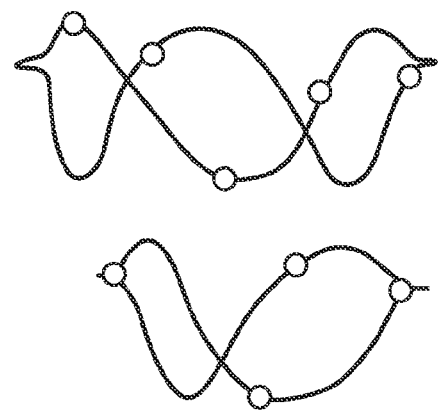
FIGS. 6D-6L show temporarily implantable surrogate systems, including catheter-based intraluminal fixation structures and/or non-tethered retrievable intraluminal fixation structures, as well as their use when deployed in lumens and/or chambers of the heart so as to provide a tracking surrogate.
Figure 6D:
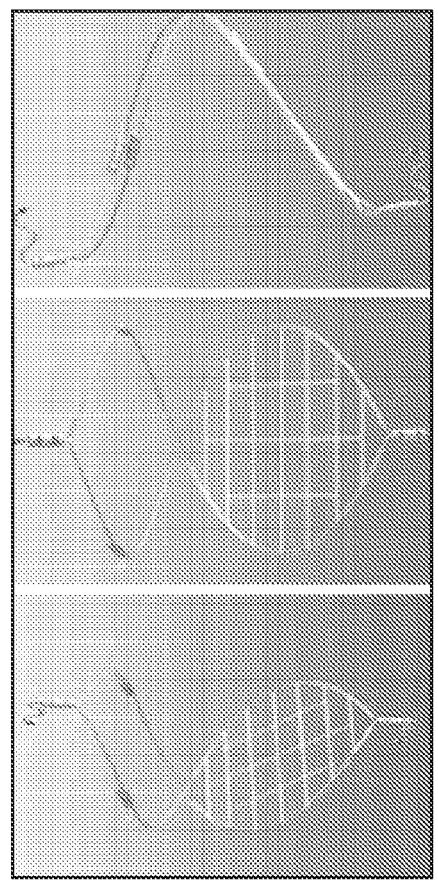

Referring now to FIGS. 6D and 6E, an exemplary non-tethered surrogate system can be understood. FIG. 6D shows a temporarily implantable fixation structure comprising two opposed helical wires coupled together. This exemplary non-tethered fixation structure can be deployed and retrieved intraluminally using catheter structures, and which can temporarily support one or more fiducials during imaging, planning, and/or treatment. The fixation structure of FIG. 6D may employ (or may be derived or modified from) a structure developed for use as a vena cava filter by Crux Biomedical Inc. of Menlo Park, Calif., and the fixation components and use of this embodiment may be further understood with reference to US Patent Publication No. 2008/0147111, published on Jun. 19, 2008 and entitled "Endoluminal Filter with Fixation," in the name of Johnson et al. (application Ser. No. 11/969,827, filed Jan. 4, 2008), the full disclosure of which is incorporated herein by reference. The methods and catheter structures used for deployment of the structure of FIG. 6D (as well as the methods and catheter strucures used for recapture and retrieval) may also be understood with reference to the '111 publication. As can be seen in FIGS. 6D and 6E, for use with the radiosurgical treatment systems and methods described herein, one or more enhanced contrast passive fiducials may be affixed (directly or indirectly) to two opposed outer helical wires or other filaments coupled together at their ends, with the crossings and couplings of the wires defining frames therebetween. Alternative embodiments may employ an active fiducial affixed to the outer helical wires, with the active fiducial optionally having a tether or being self-powered. The filter filament elements shown in FIG. 6D extending between the outer helical wires may be removed or omitted, or may remain in place in some embodiments. The crossing helical wires may define two, three, or more frames (as shown in FIG. 6E).

Figure 6F:
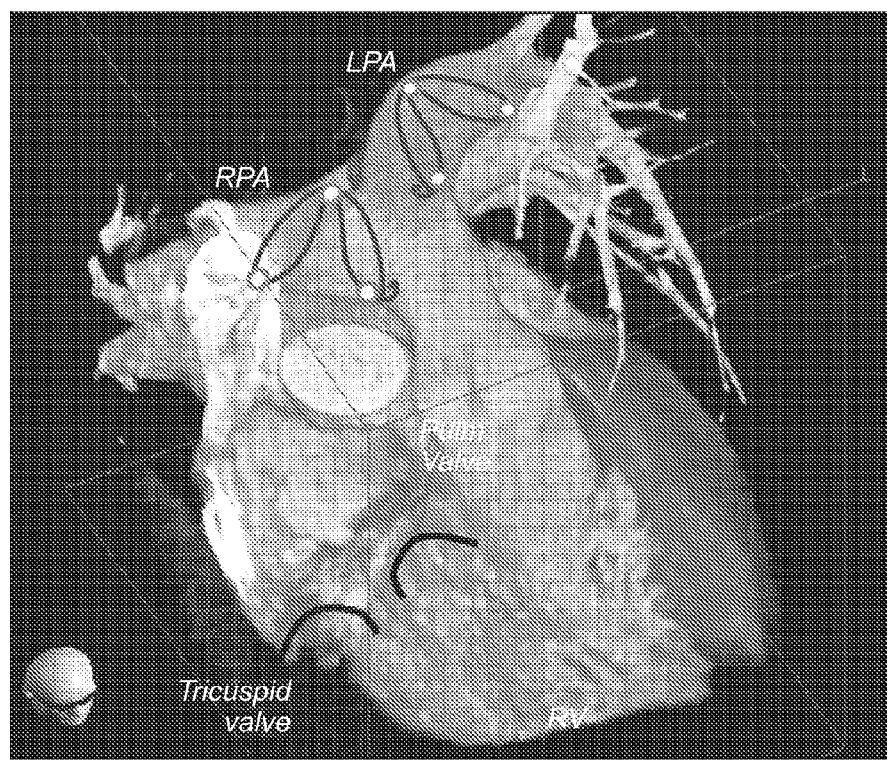
Figure 6G:
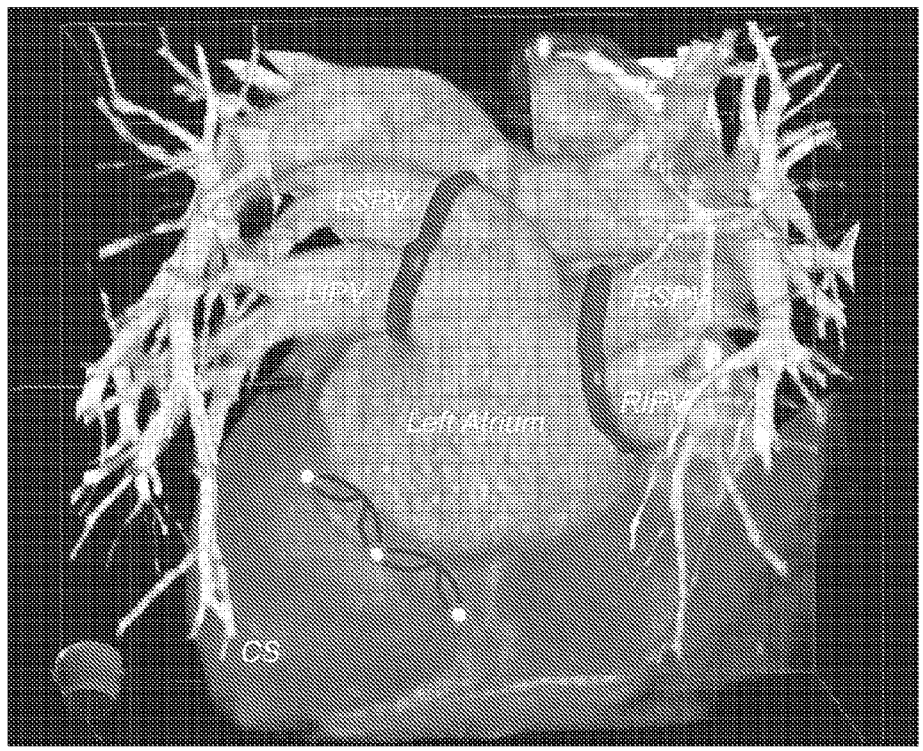

Referring now to FIGS. 6F and 6G, methods for using a surrogate system having the un-tethered fixation structure of FIGS. 6D and 6E can be understood. In FIG. 6F, two two-frame temporary intraluminal fixation structures have been implanted in the pulmonary arteries to support non-collinear fiducials so as to facilitate tracking of a moving tissue of the heart. The pulmonary valve and right ventricle are identified for orientation. In FIG. 6G, target regions encircling the left superior and inferior pulmonary veins LSPV, LIPV, and encircling the right superior and inferior pulmonary veins RSPV, RIPV, adjacent the left atrium may be tracked with the aid of a surrogate system having multiple loops or frames temporarily implanted within a coronary sinus CS. Prior to deployment, the non-tethered surrogate system can be pre-loaded inside a delivery and/or guiding catheter. An elongate flexible body (optionally a dilator) inside the guiding catheter acts as a plunger to push out the surrogate system to be indwelling inside a vessel such as the coronary sinus, inferior vena cava (IVC), superior vena cava (SVC), pulmonary arteries, or other desired vessel. A custom delivery system can also be used. Once the treatment is complete, a retrieval catheter such as a snare can recapture and retrieve the indwelling surrogate system, for example, by grabbing onto a protrusion or hood disposed at a proximal end of the fixation structure (see FIG. 6D). The fixation structure may optionally have anchors protruding radially from an outer surface of the helical wires, similar to those provided on the Crux™ IVC filter to provide better fixation to the vessel walls. To deliver a fiducial system to the pulmonary arteries, a flow-directed balloon catheter similar to a Swan-Ganz catheter may be used. Following this, a guide-wire can be inserted to the delivery site. The guide-wire may also be twisted while the flow-directed balloon is inflated to select a right or left pulmonary artery. The Swan-Ganz is then withdrawn while the guide-wire is in place, and a catheter pre-loaded with the surrogate system is advanced to the target site over the wire. The surrogate system is deployed at the target site. The guide-wire and the delivery catheter may be withdrawn, leaving the surrogate system behind. Alternatively, a flow-directed balloon can be integrated with the fiducial delivery system. Hence, the surrogate system may be tethered and/or non-tethered (indwelling).

Figure 6H:
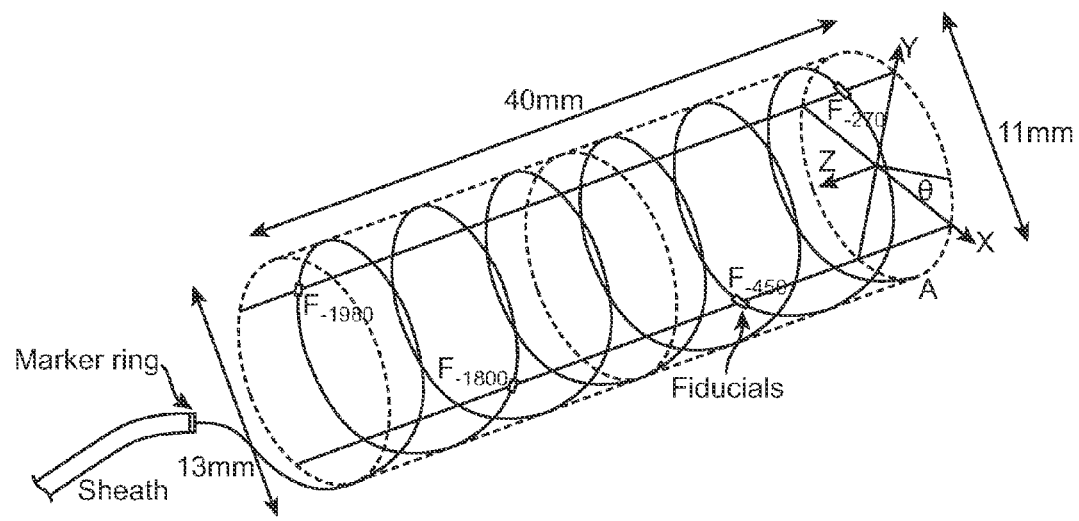
Figure 6I:
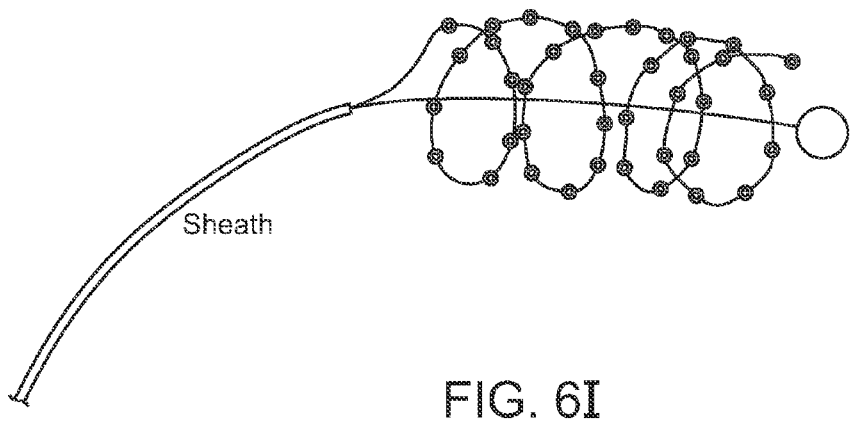
Figure 6J:
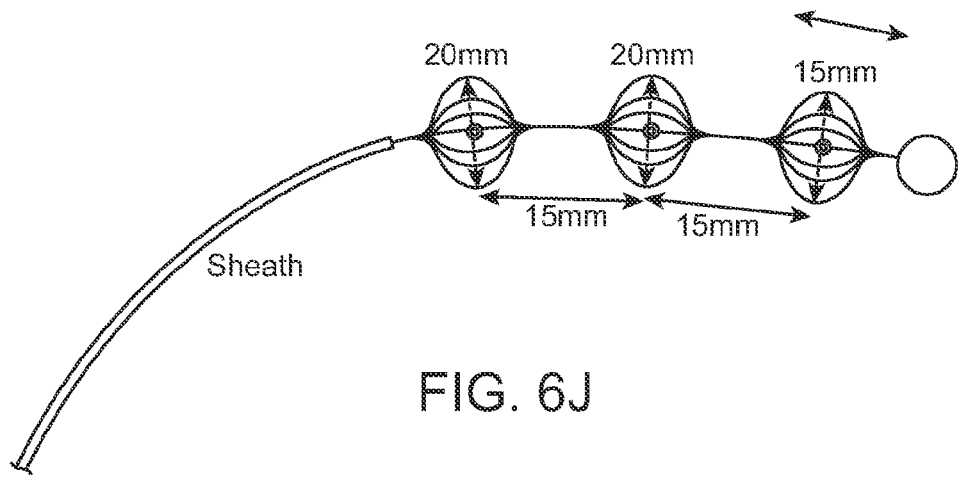
Figure 6K:
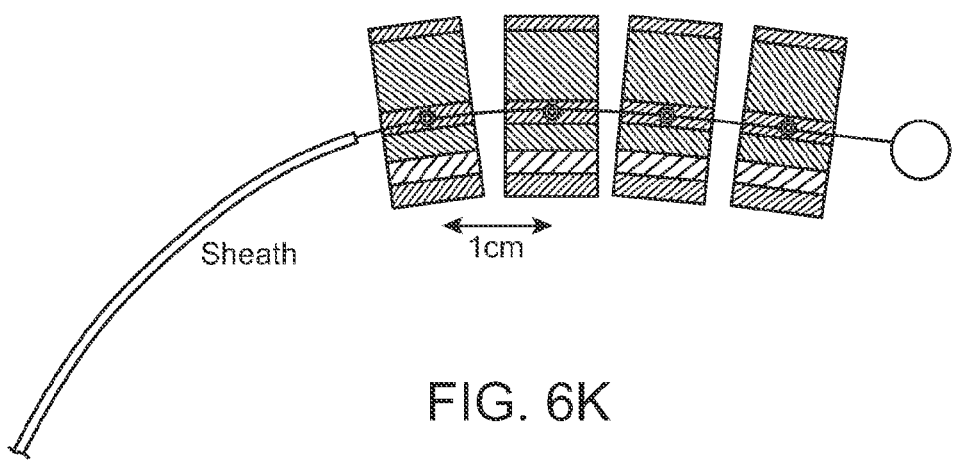
Figure 6K:
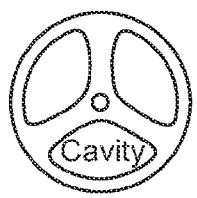
Figure 6L:
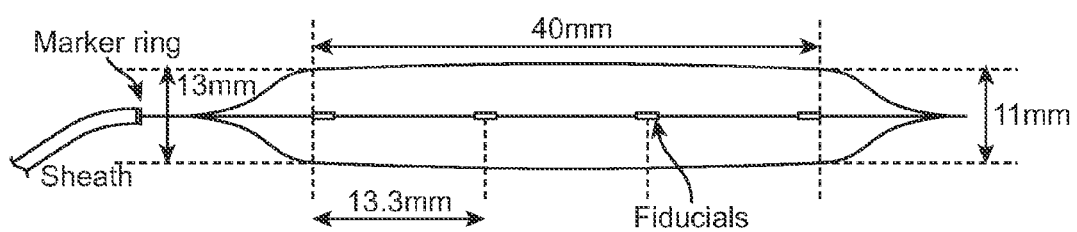

Referring now to FIGS. 6H-6L, additional alternative fixation structures are illustrated. In the embodiment of FIG. 6H, a helical stent-like fixation structure supports fiducials abutting the walls of the blood vessel in which the fixation structure is expanded, typically be releasing a helical filament structure from within an associated sheath. In the embodiment of FIG. 6I, a helical stent-like fixation structure includes a flow-directed balloon near a distal end of the surrogate system and/or deployment catheter to help guide advancement of the deployment catheter downstream within a blood vessel. Once again, the fiducials will abut the walls of the surrounding blood vessel, and the fiducials may be separated along the helical length of the fixation structure at regular or varying distances, for example, at every 1 cm. In the embodiment of FIG. 6J, an axially series of expandable basket-like structures are each defined by a circumferential series of flexible members. A pull-wire allows a length of the basket like structures to shortened and their diameter expanded in situ from outside the patient. A flow-directed balloon at the distal end of the baskets helps guide the catheter downstream, and the fiducials may remain at the center of the blood vessel when the baskets are expanded by mounting the fiducials along to the pull-wire or to another structure that remains along the center of the baskets. FIGS. 6K and 6Ki schematically illustrate a series of spoke and wheel balloons (optionally referred to as cartwheel balloons) with an optional flow-directed distal balloon to help guide distal advancement of the deployment catheter downstream along a blood vessel. Fiducials may again be mounted along a central portion of one or more of the balloons. FIG. 6L schematically illustrates an alternative expandable support structure comprising a braided tube with a fiducial-supporting pull wire disposed along a center of a braided tube. Shortening of the tube by pulling the pull wire relative to the proximal end of the tube results in radial expansion of the tube, with the fiducials remaining substantially along the center of the blood vessel.

Figure 8A:
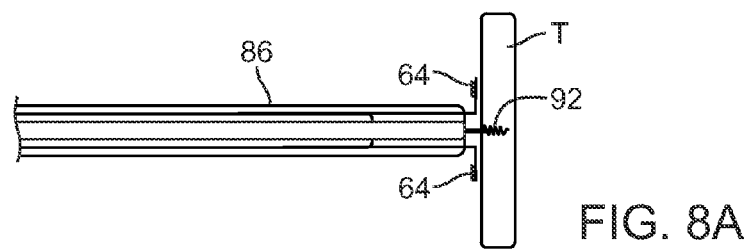
FIGS. 8A-8F illustrate alternative catheter-based surrogate systems having image-able and/or active fiducials to facilitate tracking of moving heart tissues.
Figure 8B:
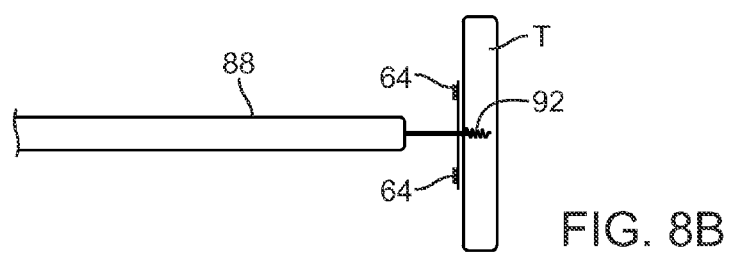
Figure 8C:
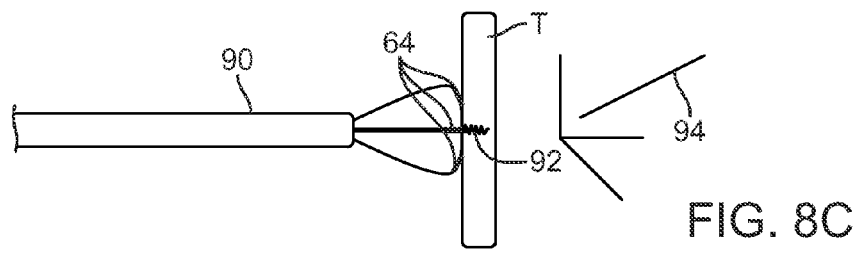
Figure 8D:
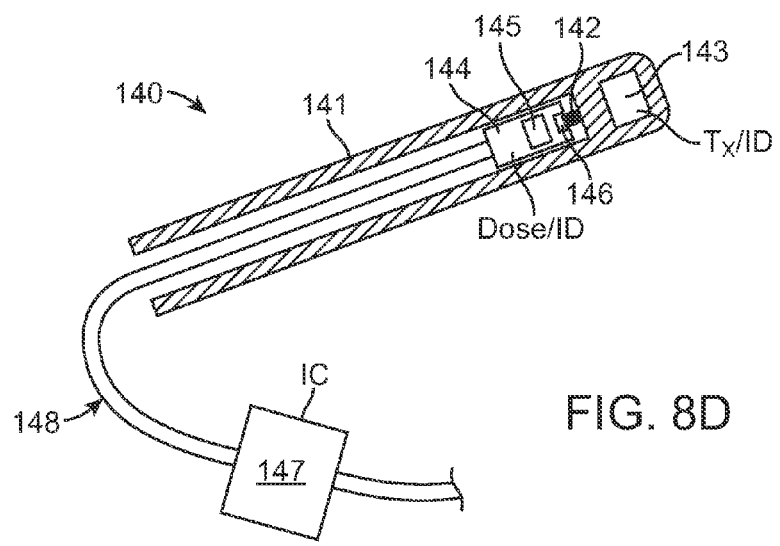
Figure 8E:
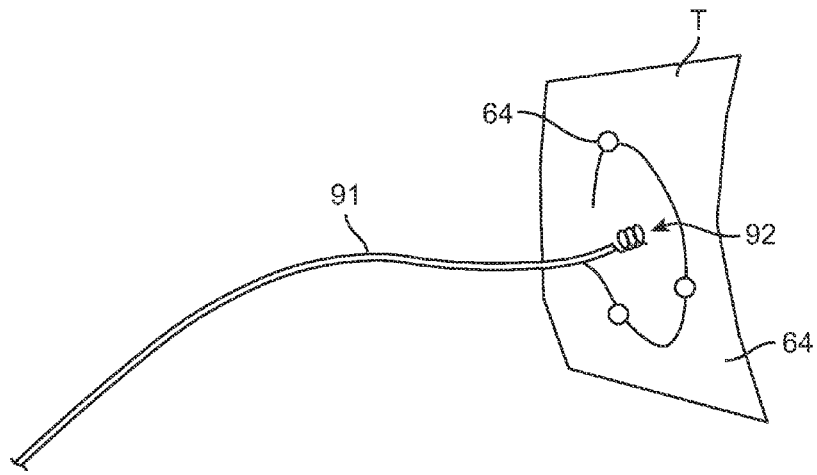

FIGS. 8A-8C and 8E schematically illustrate still further alternative catheter structures for deploying fiducials and temporarily affixing the fiducials 64 to a heart tissue T. Catheters 86, 88, 90, 91 affix fiducials 64 to tissue T using a helical screw 92 that can be screwed into tissue T by rotating the catheter about its axis, with the exemplary helical screw being similar in structure to helical cardiac pacemaker leads. Fiducials 64 are supported by resiliently or plastically flexible members, allowing the fiducials to expand from the substantially linear configuration with the surrounding sheath to a non-colinear deployed configuration in engagement with the tissue T. The non-colinear deployed configuration of fiducials 64 enhances the accuracy with which a three-to-six-dimensional offset (shown schematically by offset 94 in FIG. 8C) can be determined relative to three-dimensional or bi-plane images of the fiducials. As the target tissue may be identified using a three-to-six-dimensional offset 94 from the fiducials during treatment, this may enhance tracking accuracy. The resilient structure of catheter 91 is biased to form an a arc or lasso engaging a tissue intersecting helical screw at least partially around the helical screw. FIG. 8E shows an alternative fiducial deployment catheter 89 in which a deployable cone 89a disposed at a distal end of the catheter can be temporarily affixed to an endocardial tissue surface T by applying a vacuum within the catheter using a vacuum source such as a syringe 89b coupled to a proximal end of the catheter. A fiducial catheter 89c can then positioned adjacent the distal end of deployment catheter 89 by advancing the fiducial catheter distally through a port 89e at the proximal end of the deployment catheter. Additional monitoring or ablation devices may also be advanced distally through the port, and deployment of the cone may be effected from the proximal end of the deployment catheter using an actuator 89f. Fiducials 89d may be mounted to or near the distal end of fiducial catheter 89d.

A still further alternative catheter-based fiducial structure which may be adapted for use in the present invention is shown in FIG. 8D, and is described in more detail in U.S. Patent Application 2008/0292054, entitled "Device for Measuring Administered Dose in a Target" (the full disclosure of which is incorporated herein by reference). While the exemplary embodiment described in that reference comprises a urethral catheter for facilitating treatment of prostate cancer, a similar structure might be modified by inclusion of a helical screw 92 or stent-like structure 68 as described above regarding FIGS. 8A-8C, 8E, and FIGS. 6A-6C. Some embodiments may include the dose measurement components of catheter 140 shown in FIG. 8D, although many other embodiments will omit dose measurement capabilities. Regarding exemplary catheter 140, that structure includes an elongate flexible catheter body 141 provided with an electrical guide 142 and an electrical marker 143. The marker comprises a transmitter $T_x$ used to determine the position of a target area in a patient and in identification ID of the patient. The implant further comprises a combined dose and identification unit 144 having a dose sensor 145 used to detect the amount of administered dose in the target area and a dose identification Dose/ID.

The combined dose and identification unit 144 is provided with a connector 146 that is arranged to be connected to electrical guide 142, and can ensure the correct unit 144 is connected by comparing the dose identification Dose/ID and the ID of the patient in the electrical marker 143. The transmitter $T_x$ may be powered through the combined dose and identification unit 144 so as to verify position of the catheter 140, since movement of the catheter (and tissue to which the catheter is attached), determine an offset between a transmitter signal-based position of the catheter and an image-based location of the catheter, and the like. The combined dose and identification unit 144 is connected to an externally arranged integrated circuit 147 through wires 148, and the integrated circuit 147 includes the functionality associated with dose conversion as more fully described in U.S. Patent Publication 2008/0292054. Suitable alternative active fiducials often rely on electromagnetic or ultrasound transmission to or from the fiducial so as to identify a location of the fiducial (independent of any imaging system obtaining an image of the implanted fiducial with or without the surrounding tissue). Suitable electromagnetic position sensing structures may be commercially available from a variety of suppliers, including the Carto AcuNav™ catheter available from Biosensewebster, the various three-dimensional guidance tracker structures commercially available from Ascension Technology Corporation of Vermont, the ultrasound sensor and systems commercially available from Sonometrics Corporation of Canada, the EnSite™ cardiac mapping system from St. Jude Medical of St. Paul, Minn., and the like. These active fiducials send and/or receive signals indicating a position of the fiducial, movement of the fiducial, and the like, with this signal being used as an input into the processor of the radiosurgical treatment system for tracking of the target tissue.

The fiducials, fixation structures, and/or surrogate systems described herein (and optionally those embodiments which expand radially from a low-profile insertion configuration to a temporarily affixed configuration radially engaging a surrounding lumen wall) may be attached in and to one or more of the following: the coronary sinus, left pulmonary artery, right pulmonary artery, pulmonary artery trunk, right ventricular outflow tract, inferior vena cava, superior vena cava, pulmonary veins, left ventricular outflow tract, aortic arch, ascending aorta, descending aorta and coronary arteries, as well as in and/or to other tissue structures of the heart. In other embodiments of surrogate systems (optionally including those employing screw-in affixation devices and/or vacuum affixation) can be attached to the walls of the right atrium, atrial septum, left atrium, right atrial appendage, left atrial appendage, right ventricle, ventricular septurm, and left ventricle. Still further alternative embodiments may be employed, including deployable or fixed annular rings supporting fiducials and which may be fitted to the tricuspid valve annulus, mitral valve annulus, pulmonary valve annulus, and/or aortic valve annulus.

As the treatment plan will often have been developed before the fiducial implantation, tracking of the target tissue will be easier once the location of the fiducial relative to the planned target has been identified. A process for registration a treatment plan with implanted passive and/or active fiducials can be understood with reference to FIGS. 7, 10, and 11.

Figure 10:
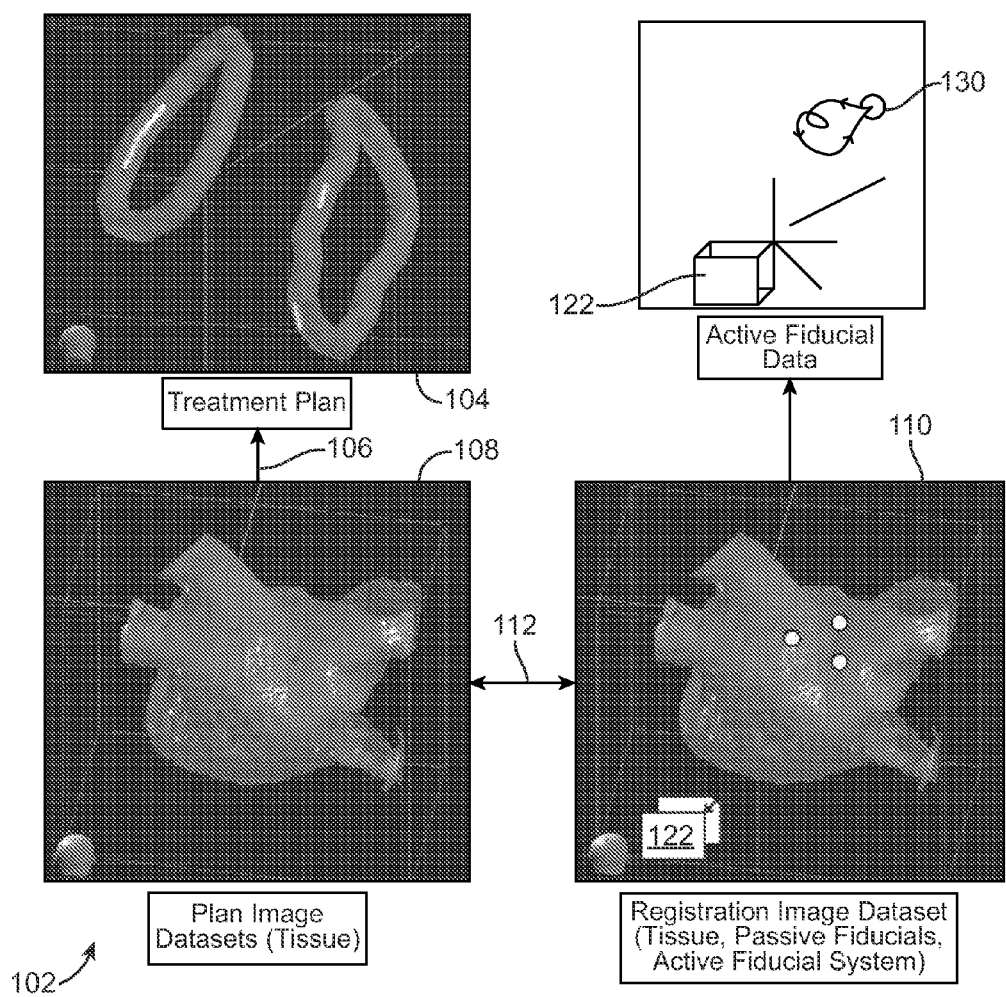
FIG. 10 schematically illustrates registration of implanted catheter-based active and/or passive fiducials with a treatment plan.
Figure 11:
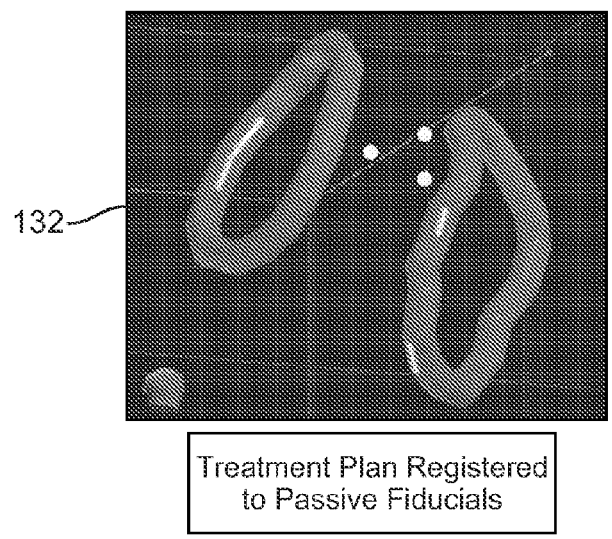
FIG. 11 graphically illustrates a registered treatment plan and passive fiducial system.

As a starting point, a treatment plan 104 preferably has a known positional relationship 106 with planning image data 108 (these elements being shown schematically in FIG. 10). Relationship 106 can be established by inputting the desired lesion pattern relative to an image generated using the planning image data, as described above. So as to identify a location of fiducials 64 relative to the treatment plan 104, registration image data 110 may be acquired after fiducial implantation 70. Registration image data 110 will typically comprise three-dimensional image data encompassing both the heart tissue and at least some of the implanted fiducials, particularly the passive high-contrast fiducial marker structures. Identification of tissue surfaces and the like may again be facilitated by releasing contrast in the bloodstream. This facilitates segmenting the heart tissue surface and the heart/blood interface. The tissue/blood interface within the chambers and adjacent vessels of the heart from registration image data 110 and planning image data 108 may be used to identify a relationship 112 between the plan image data set and the registration image dataset. The exemplary relationship 112 may comprise a mapping or transformation, ideally comprising a transformation matrix, offset, or the like. Rather than relying on the blood/tissue interface, alternative image/registration relationships 112 may be determined by identifying a series of discrete tissue landmarks such as an apex of a chamber, a valve ring plane, an ostial center and orientation of a blood vessel, a bifurcation location, or the like. Note that the heart tissue may move significantly between acquisition of the planning image data set 108 and the acquisition of the registration dataset 110 relative to anatomical landmarks outside the heart, and that the shape of the heart and/or its components may be deformed (even at similar phases of the beat cycle). Hence, while embodiments of the invention may employ a simple rigid transformation as the plan/registration image relationship 112, other embodiments may employ any of a variety of deformable registration techniques.

So as to facilitate identification of the plan/registration image relationship 112, registration image dataset 110 may be acquired using an image modality which is the same as that used to acquire planning image dataset 108. For example, where the planning image dataset comprises CT data, registration image dataset 110 may also comprise CT data. Alternatively, if MRI data has been used for the planning image dataset 108, MRI acquisition after fiducial implantation may be used for the registration image dataset 110. Similarly, if the planning image dataset 108 comprises ultrasound data, the registration image dataset 110 may also comprise ultrasound data. Nonetheless, other embodiments may employ a different image modality to acquire the registration image dataset than that used for acquisition of the planning image dataset. Any of a wide variety of three-dimensional image data fusion, three-dimensional rigid transformation, and/or three-dimensional deformable transformation techniques may be used despite the application of different imaging modalities.

In exemplary embodiments, the registration image data 110 may include at least one component of an active fiducial system. For example, FIGS. 9A, 9B, and 10 illustrate a method and system for registering a catheter tip with a three-dimensional image dataset (such as CT data) with high absolute accuracy. Standard active catheter navigation systems may suffer from geometric distortion due to either magnetic field inhomogeneities or assumptions in electrical impedance. Analogous errors may be present in ultrasound or other navigation systems. While these tracking technologies provide good relative position measurements with respect to, for example, an image-able electrode in the coronary sinus, their absolute accuracy may not be as good as is desirable for radiosurgical treatments from outside the body.

FIGS. 9A and 9B schematically illustrate a transmitter 122 of an active fiducial catheter navigation system, with the exemplary transmitter shaped as a cube. The active fiducial may comprise a sensor disposed near the distal end of the catheter that senses the location of the position fiducial. The reference coordinate system of the active fiducial may be positioned at a corner of the cube-shaped transmitter 122. Alternative systems may replace this external transmitter with an external sensor, with the active fiducial comprising an associated transmitter. Regardless, the patient may lie on a patient support 124, and the patient support may also support the external active fiducial sensor 122 or transmitter. In some embodiments, the patient support 124 may comprise a vacuum bag or other structure so as to inhibit movement of the patient relative to the patient support, and the patient support may be movable (with the patient and the component of the navigation system mounted thereon).

The movable patient support 124, active fiducial transmitter 122, and patient are positioned for imaging, such as by being placed on a couch of a CT scanner 126. As a result, the registration image dataset (an image of which 128 is shown in FIG. 9B) contains the transmitter cube 122, such that the transmitter cube is visible in the CT dataset along with the patient's tissue and any other implanted fiducials.

In some embodiments, the patient support 124 and patient may be moved to an electrophysiology lab and placed on a platform or electrophysiology table, with the vacuum bag of the patient support 124 inhibiting movement of the patient relative to transmitter 122. A catheter having the active fiducial position sensor may be introduced into the patient and advanced to the heart tissue, allowing the active fiducial navigation system to determine position data from the active fiducial. As the position of the sensor 122 in the CT dataset is known, and location and orientation of the active fiducial navigation system is also known, and an active fiducial marker can be superimposed on the CT image dataset location identified by the navigation system of the active fiducial. Hence, a relationship between the active fiducial 130 and the tissue, passive fiducials, and treatment plan 104 may also be identified (see FIG. 10). By correlating the active fiducial position information with the phase of the heart, and by knowing a relationship of the target region to the active fiducial location throughout the heartbeat cycle (as can be determined from the time series of three-dimensional datasets in the planning image data), the active fiducial data signal may enhance tracking of the target region.

As a result of the registration step 102, the three-dimensional position offset (or transformation matrix or matrices) between the fiducials and the treatment plan may be determined, so that the fiducials are effectively registered with the treatment plan 132.

Referring now to FIG. 9C, a block diagram of an exemplary calibration module 200 indicates an alternative system and approach for helping to register the patient tissue with a treatment plan, and/or for helping to align the patient with the radiosurgical treatment system. Calibration can, for example, be performed prior to delivering a treatment either before the patient is present on the patient support 24 or once the patient is on the patient support 24 of the radiosurgical system 10. Calibration can determine the mapping function, φ, between a coordinate system of an active fiducial system (such as a tracking coordinate system of an Ascension Technology Corp. 3D tracking system) and a coordinate system of radiosurgical system 10 (such as a CyberKnife™ radiosurgical robot coordinate system):

$$^{CK}p = \Phi(^{AS}p),$$ Eq. 1 where, $^{CK}p$ is a point in robot coordinate system and $^{AS}p$ is the same point in the active fiducial tracking coordinate system. The mapping function φ can be determined, for example, by moving an active fiducial (typically in the form of one or more position sensors) to a series of locations, ideally to a series of grid points inside a volume of interest. The grid points and/or volume of interest may be centered at or near an isocenter of the planned treatment and/or of the robot 14 supporting the linear accelerator 12 (or other radiation source). When using the exemplary CyberKnife radiosurgical treatment system, the treatment isocenter may be a point in the CyberKnife room where the axes of the two ceiling-mounted tracking cameras intersect. This may also be used as the origin of the CyberKnife coordinate system. The movement of the active fiducial between the locations or grid points may be performed using a motion platform Ω robot 202 (a separate robot manipulator for mechanically moving the active fiducials in an near the treatment site), and locations of the active fiducials may be sensed and recorded by the tracking module 206 based on both the active fiducial tracking system 204 and also the image tracking system 16 (such as the CyberKnife™ X-ray system). A least squares fit between the image tracking-based positions and the active fiducial-based positions can be used by the calibration module 206 to find the best-matching mapping function, φ.

A Calibrator 208 is a component of calibration module 206. Calibrator 208 will interact with a server application running on the radiosurgical system, called CHServer. CHServer will serve some requests from Calibrator 208, by communicating via an Ethernet. Calibrator 208 is also connected to the active fiducial motion platform, ΩRobot 202, and the active fiducial tracking system 204, both via USB. Calibrator 208 may:

Instruct the ΩRobot to move the sensors to a specified location

Instruct the image tracking system 16 of the radiosurgical system to acquire a pair of X-rays.

Capture active fiducial sensor coordinates for the present location

Download the X-rays via CHServer.

Repeat steps 1-4 until all grid points or otherwise desired locations have been visited. Once the data from all grid points have been captured, Calibrator 208 will compute the mapping function, φ, and store it in a file.

Figure 12:
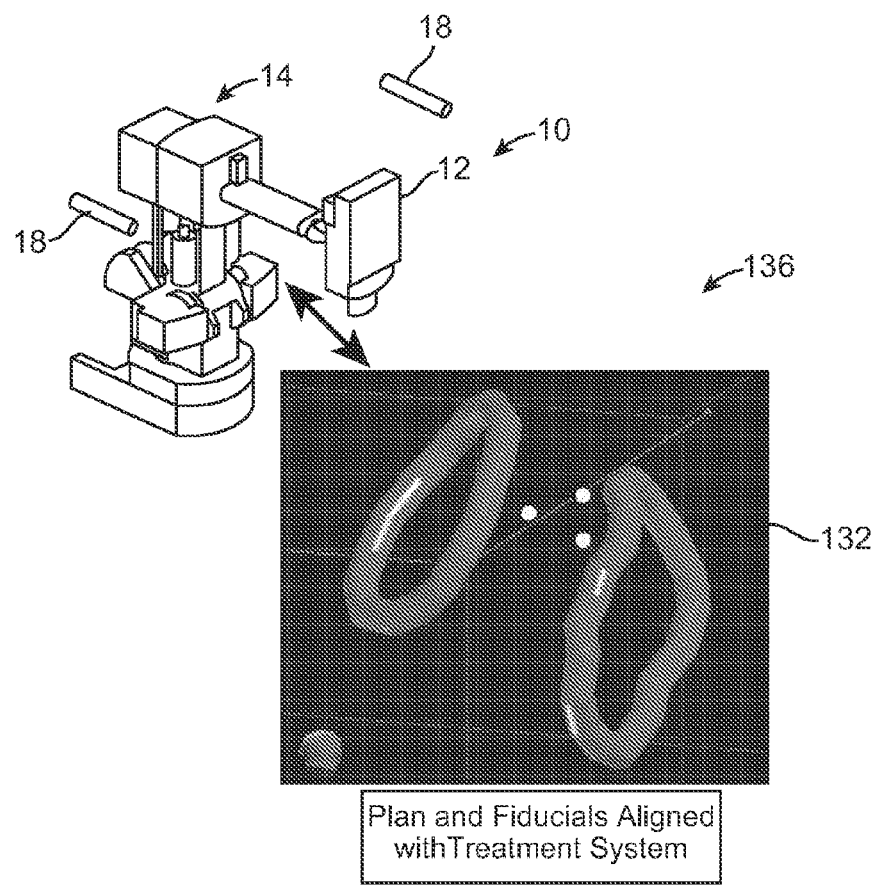
FIG. 12 graphically illustrates alignment of the treatment plan with the treatment system.

Referring now to FIGS. 7, 12, and 1, alignment 136 of the target regions of the tissue with the robot 14 will generally be performed by having the patient supported by patient support 24, and by moving the patient support using the articulated patient support system 26 so that the fiducials (as seen in the bi-plane X-ray images of image guidance system 16) are disposed at the desired location, such that the target regions of the treatment plan are aligned with the planned trajectories from linear accelerator 12. Hence, although the fiducials have in fact been implanted after the treatment plan was completed, the alignment process may proceed with reference to superimposed fiducial locations on the planning treatment data, with the alignment process, as it appears to the medical personnel performing the radiosurgical treatment, being quite similar to that applied when a pre-planning fiducial is used.

Figure 13:
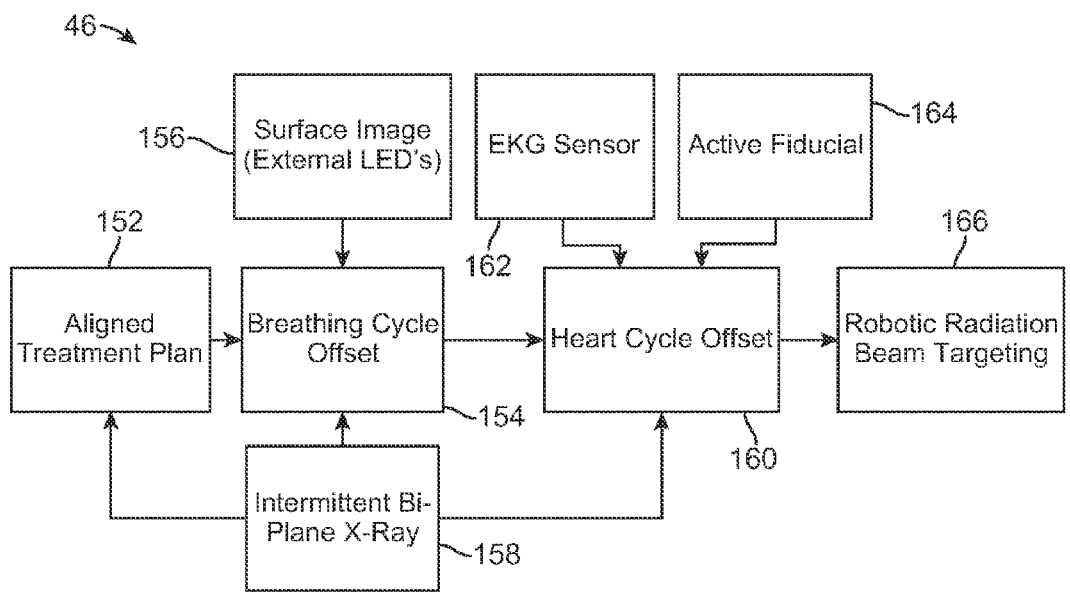
FIG. 13 schematically illustrates a method for treating a target region according to a treatment plan.

Referring now to FIGS. 7 and 13, the treatment 46 and tracking of the target tissues by the robot and linear accelerator can be generally understood. The aligned treatment plan 152 (including the planned trajectories and the superimposed fiducials, once they have been appropriately aligned with the robot 14 as described above with reference to FIG. 12) defines appropriate trajectories and beams of radiation from linear accelerator 12. As with known radiosurgical treatments, an offset is determined to compensate for the breathing cycle 154, with the breathing offset generally being determined from the respiration amplitude as identified using surface images of the patient, and specifically from external LEDs mounted on the patient's skin 156. Intermittent bi-plane X-ray data 158 can be used to revise and correct the breathing motion offset for any patient movement or the like.

A heart motion offset 160 may also be applied to the treatment plan 152, with the phase of the heart cycle offset being identified by an EKG sensor 162 or other heart cycle monitor coupled to the patient. Data or signals from the active fiducial 164 may also be used to identify the phase of the heart motion, as well as providing an appropriate heart motion offset. The heart cycle offset throughout the heart cycle may, as explained above, be identified from the time series of three-dimensional datasets included in the treatment plan 152. Alternatively, the EKG sensor signals 162 and/or active fiducial signals 164 may be used for gating of the radiation beams, such that the radiation beams are only directed toward the heart tissue at portions of the heart cycle during which the target regions are sufficiently aligned with the plan 152. Note that some portion of the heart cycle motion of the tissues located at the target regions may be disregarded, for example, with internal deformation of the tissue between the fiducials and the target regions being disregarded in favor of a fixed offset, with motions in one or more orientations having a sufficiently limited amplitude being disregarded, or the like. Regardless, once the appropriate offsets have been applied to the treatment plan, the robotic radiation beam targeting 166 can then be applied.

Figure 12A:
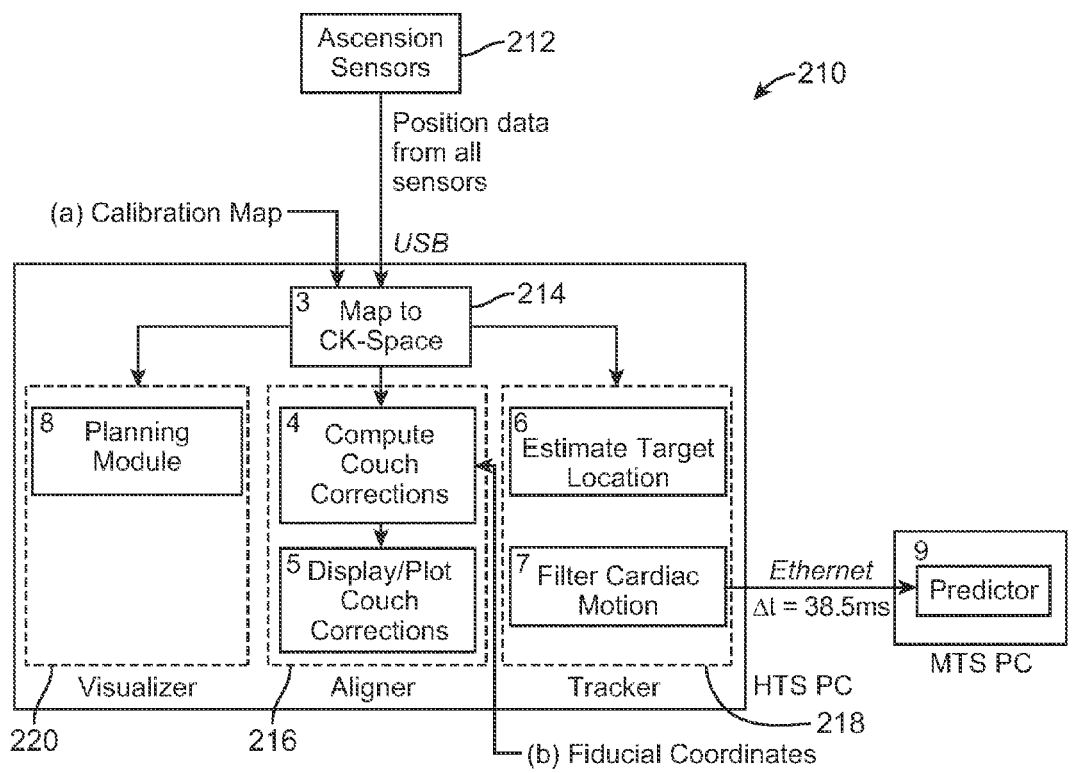
FIG. 12A is a functional block diagram schematically illustrating an embodiment of an active catheter tracking module.

Referring now to FIG. 12A, a tracking module 210 using components and techniques related to those of FIG. 9C can now be understood. For convenience, we can here assume that the alignment center in the planning CT data is disposed at a center of gravity of the fiducials. As this will often not be the case, offsets between the planning data and fiducial centers will typically be included. Tracking module 210 includes software run on a heart tracking computer HTS during treatment delivery. The alignment module 206 may similarly run on the heart tracking computer HTS, with the tracking module and alignment module comprising code running on a personal computer (PC) in the exemplary embodiment. The tracking module 210 receives as input the position data 212 from all the active fiducial sensors (such as the Ascension sensors) of the implanted catheter system via USB. Tracking module 210 applies the calibration map 214, $\phi$, to this active fiducial data to compute the active fiducial locations in the coordinate system of the radiosurgical system (such as in CyberKnife™ coordinates). From this, the position data flows into 3 different paths: an Aligner 216, a Tracker 218, and a Visualizer 220.

Aligner 216 makes use of the data from the active fiducials to alter alignment of the patient with the radiosurgical system. More specifically, the active fiducial sensor data can be matched in aligner module block [4] to the fiducial coordinates from the planning CT data (specified in radiosurcial system coordinates) to determine the couch corrections. The average couch correction over a specified period can be computed and displayed to the user. The user can then apply these couch corrections and observe how couch corrections change in real-time. The block [5] may display the couch corrections to the user in a graphical form, computed as running averages.

Tracker 218 may include a tracker module block [6] configured to compute the target location from the incoming active fiducial locations. After alignment the alignment center of the patient, as defined in the planning CT coordinate system, coincides with the iso-center of the radiosurgical treatment system. If there is no motion, the output of block [6] might be (0, 0, 0). If there is motion, the output of block [6] might be the change in position from the initial or ideal position. A tracker module block [7] may remove the cardiac motion from the target motion. The resulting 'respiration only' change-from-ideal motion waveform can be sent to a position predictor of the radiosurgical treatment system processor, which can apply this information per a standard data path to drive the robot.

The active fiducial data may be provided to visualizer 220, which may display the fiducial locations superimposed on CT data, optionally using display module components of the planning module. This may allow the system user to visualize the locations of the active fiducials after they have been implanted, and the like. In addition, the visualizer may display the treatment beams fired by the robot in real time using the position data measured using the active position sensor.

As can be understood from the above, patient movement complicates radiation treatment of diseases of the heart. If patient movement is not tracked, targeting can direct the beams into a time average location of the target. If a surrogate and target are rigidly coupled together and tracking of the surrogate is accurately maintained, targeting is not compromised. However, when the surrogate is offset from the target and the tissue in which the target and surrogate are disposed deform, and if the deformation between the surrogate and target are not tracked, a single imaging phase can be used to calculate the relative location of the surrogate and target. Selection of the appropriate imaging phase (from among the time series of phases at which three-dimensional imaging is acquired) can affect the accuracy of targeting. For example, if a calculation of the relative locations is performed for a phase where the surrogate to target offset is not close to the average offset throughout the heartbeat cycle, targeting based on an average surrogate location may result in dose delivery being offset from the target.

One relatively simple approach to accommodate untracked motion is to use an integration of the target volume so that the target is expanded to include the target region location throughout all phases of the target region motion (including throughout a heartbeat cycle and/or respiration cycle). Such an integrated target can ensure treatment of the target region but may increase the total treatment volume receiving relatively high doses of radiation. Alternative pursuit tracking approaches (similar to those used in the Accuray Synchrony™ tracking system) where the radiation beams move synchronously with the target tissue can be used in order to deliver dose to the target region. These existing approaches may not consider motion of radiation sensitive collateral tissues, nor motion of the surrogate relative to the target region. Gating of the radiation beam to untracked motion can also be employed, but may increase the total time to provide a sufficient dose to the target region.

In an exemplary alternative untracked treatment approach, the tissue may be analyzed as being subjected to the dose that is integrated across an untracked tissue motion. The peak dose may be delivered to the average position with some alteration of the dose distribution in areas where the dose gradient is changing in the direction of motion. For motions which are relatively small relative to the rate of change of the dose gradient, the dose distribution may only be slightly altered by the untracked motion. The more significant change between the intended dose and that actually applied to tissue may be imposed by any shift of the peak dose from its planned anatomical locations.

In this exemplary targeting approach in the presence of untracked motion, imaging of the tracking surrogate may be used to direct the radiation beams. If only a single image of the tracking surrogate is obtained there will be targeting errors resulting from the untracked motion, so that intermittent acquisition of images allow the location data to be combined so as to determine future beam directions, preferably by averaging so as to better locate the tracking surrogate. This approach may result in the beams being directed relative to the average location of the tracking surrogate relative to the target region. If the plan has been created based on this same average relative positioning, the peak dose location should correspond to the planned target region.

In light of the above, and as can be understood with reference to FIGS. 14A-14E, targeting accuracy can be enhanced in the presence of untracked motion by analysis of a time average location of the target relative to the tracking surrogate throughout cardiac and/or respiratory motion. One relatively simple method is to use this time average relative location during planning by selecting the phase where the tracking surrogate is nearest to its average relative location. Note that the precise location of the surrogate may not be known during planning, but the target structure within the heart corresponding to the target locations for fiducial implantation may be identified, so that the surrogate may be targeted for deployment at or near a location appropriate for the planned average offset. The planning phase can be chosen based on the average location of the target surrogate location relative to the target structure location.

Note that no discrete phase, as selected from the time series of three-dimensional planning datasets, may correspond exactly to the time average location. Some targeting error may remain because of this difference. Additionally, the average location of the tracking surrogate may not correspond to the average configuration of the target relative to the tracking surrogate. A somewhat more accurate solution may be to consider the time average relationship between the surrogate and the target. As shown in FIGS. 14A-D, this time average may not correspond to any particular phase in the captured time series. Nonetheless, it may be convenient and beneficial to select the closest phase to the calculated time average.

Addressing FIGS. 14A-D an example of two-dimensional relative motion between a tracking surrogate (represented by the filled circle) and the target (represented by the open circle). FIGS. 14A-D show the location of the target and circuit relative to a reference frame in four phases of the cyclical cardiac motion. Both the surrogate and the target move relative to the reference frame, but the target also moves relative to the surrogate.

In FIG. 14E, a calculated average target center may provide accuracy advantages. The relationship between the average target center and the tracking surrogate does not necessarily match any of the discrete images of FIGS. 14A-D, but instead the configuration corresponds to an average separation between the objects.

In many radiosurgical systems, a CT volume set is used to create digitally reconstructed radiographs (DRRs). During treatment, guidance images are matched to these DRRs in order to align the patient. A DRR can conveniently be constructed from any one of the datasets for a particular phase of the time series. Hence, the target itself may be somewhat difficult to identify in the DRR, which provides motivation for use of a tracking surrogate. The offsets used to target the beams can, nonetheless, be based on the average target location of a DRR generated from a selected phase which most nearly matches the time average relationship. Alternatively, the relative location of the target and offset may use a calculated time average without relying on the DRR, so that the target location of the target in the CT volume may not correspond to a particular DRR. For example, if you have fiducial coordinates f(k,t), then the distances linking the fiducials are: d(k,m,t)=|f(k,t)−f(m−t)|. There will be $$M = \frac{N}{2}(N-1)$$

such link distances between fiducials, where N is the number of fiducials. The link distances can be represented as: {d(k, m,t)}, which is a M dimensional vector. Then the time average distances can be computed as: $\{\hat{d}(k,m)\}$. Then compute the vector distance:

$$\Delta(t) = \sqrt{\sum_{\forall \frac{N}{2}(N-1) values} \left(d(k, m, t) - \hat{d}(k, m)\right)^2}.$$

Then pick the phase corresponding to the smallest Δ(t)

Figure 15A:
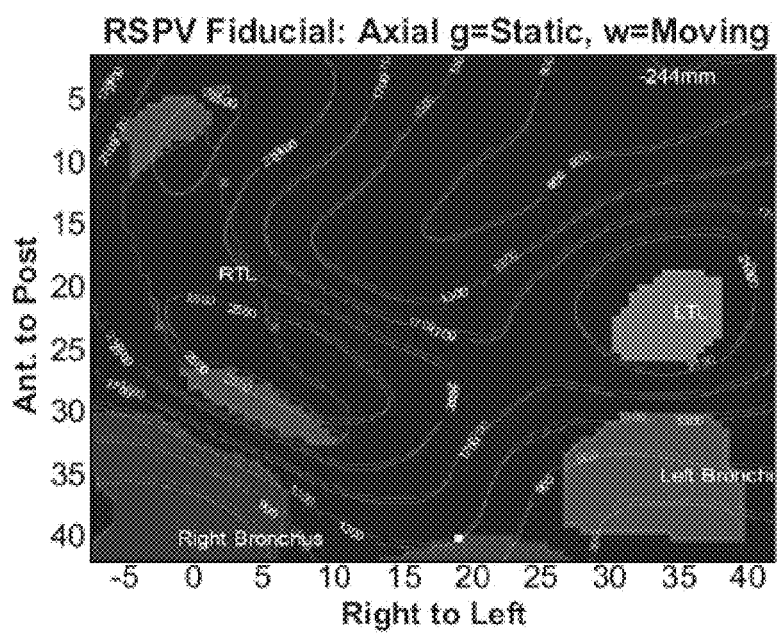
FIGS. 15A and 15B graphically illustrate the effect of motion on a treatment plan when a fixed offset is applied (in FIG. 15A) and when it is not applied (FIG. 15B)
Figure 15B:
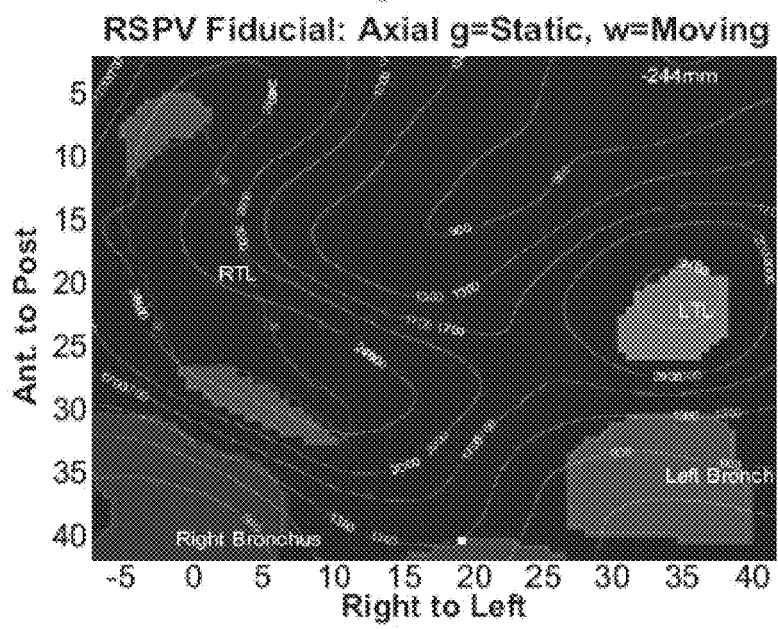

Referring now to FIGS. 15A and 15B, an effect of untracked motion on a treatment plan is graphically illustrated. These figures show the effect of the measured motion of a fiducial attached to the right superior pulmonary vein of a dog on a treatment plan meant to electrically isolate the pulmonary veins. The target lesions are shown in red (right target lesion, RTL) and green (left target lesion, LTL) while radiation-sensitive collateral tissue structures are shown in purple (right bronchus), olive (left bronchus) and blue (esophagus). The dose planned without consideration of motion is shown in green contours while the dose calculated after considering the effect of motion is shown in white contours. FIG. 15A shows the effect of dose when there is repetitive untracked motion of amplitude of 6 mm peak-to-peak in addition to a planning offset caused by selecting a phase where the offset between the fiducial and the target is different by the average by 0.5 mm. FIG. 15B shows only the effect of the repetitive untracked motion without the offset. The effect of the offset is much greater than the effect of the untracked repetitive motion.

Figure 16:
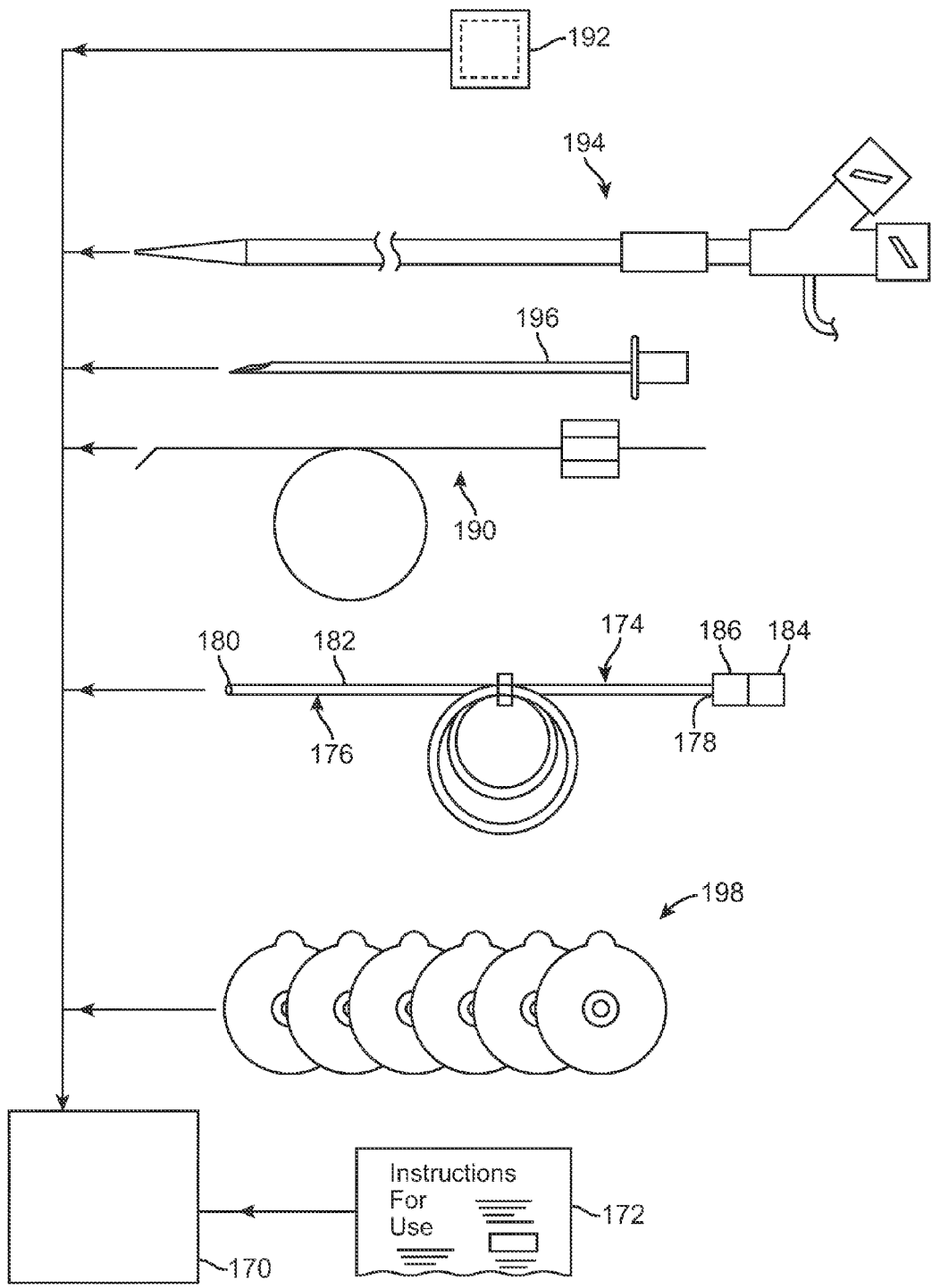
FIG. 16 schematically illustrates a kit for use with the systems and methods described herein for treatment of non-tumerous diseases of the heart.

Referring now to FIG. 16, a kit of components will facilitate radiosurgical treatments using the systems and methods described herein. These and/or other components may be included in one or more hermetically sealed packages 170, along with instructions for use 172 of the enclosed components and/or the system in general. The kit will preferably include all disposable items used during insertion of a percutaneous catheter into the heart. The catheter 174 will generally have an elongate flexible body 176 extending between a proximal end 178 and a distal end 180. A sheath 182 may have a lumen receiving the catheter body 176, the sheath optionally restraining fiducials in a small profile configuration suitable for insertion and positioning, and the sheath optionally also enclosing a helical or radially expandable fixation structure as described above. Proximal hubs 184, 186 of the sheath and catheter may allow the sheath to be withdrawn proximally from over the catheter body 176, optionally using a rapid exchange approach. Similarly, the catheter may have a rapid exchange guidewire lumen for receiving a guidewire 190, or may have a through lumen for using the catheter in an over-the-wire approach. Furthermore, the catheter may have a flow-directed balloon at the distal end, which will facilitate rapid deployment of the catheter downstream into a target site such as the pulmonary artery. While the catheter may be inserted prior to the planning image acquisition and throughout the radiation treatment, the catheter will typically be deployed on a treatment day after image acquisition and treatment planning is complete.

As described above, the catheter can include passive fiducials which include high-contrast markers that can be readily visualized during radiosurgical treatments so as to provide a passive surrogate. Alternatively, catheter 174 may include an active fiducial which transmits or receives signals electronically, ultrasonically, electromagnetically, radioactively, or the like so as to indicate a position of the catheter (and via a known relationship between a position of the catheter and the target region, thereby indicating a position of the target). Passive fiducials may comprise, for example, small metallic structures comprising gold, platinum, iridium, and/or tantallum, or the like. The catheter may also include sensors for measuring the dose received during treatment, blood pressure, and other biometric signals.

Reviewing some exemplary components included within one or more sterile packages 170, the kit may include an iodine or other skin cleansing lotion 192, a vial of 1% xylocalne, or the like. These materials may be used to create an anesthetic skin wheal at the site of skin puncture. An introducer sheath 194 may include at least one or possibly two side ports so as to allow for blood withdrawal, infusion of multiple simultaneous drugs, and other intravenous maintenance solution transmission. Exemplary introducer sheath 194 has two ports or channels so as to allow two catheters to be positioned simultaneously. A rubber diaphragm may be found at the entrance of each port, with an exemplary introducer having a 3 mm cotton tubular cuff that is impregnated with a compound comprising silver can be advanced to the site of skin puncture along a sheath of the introducer for use as a bacteriostatic.

A needle 196 allows, when used in combination with guidewire 190 and sheath 194, venous cannulation and secure positioning of catheter 174. A set of EKG electrodes 198 allows for tracking of cardiac rhythms, while a set of LEDs or gold fiducials may be mounted to the chest wall for monitoring respiration. A conductor may extend along catheter body 176 so as to couple a helical fixation lead or other conductive distal structure to engage the cardiac tissue with a proximal connector of proximal hub 186. This may allow the fixation lead or other conductive structure at the distal end of the catheter to be used as a heart signal electrode for monitoring the heartbeat, alone or in addition to the other EKG electrodes. The kit package 170 may also include a patient mattress, ideally a mattress configured to limit changes in patient position such as a vacuum bag mattress, with the vacuum bag optionally having a vacuum port and/or containing discrete pellets so as to reconfiguring and affixing of a shape of the bag once the patient has been comfortably positioned on the patient support.

In use or during deployment of the catheter-based fiducial system, needle 196 (such as a 20-gauge locator needle) may be used to identify an internal jugular vein, subclavian or brachial vein. A 14-gauge needle (not shown) also to be included in the kit and within package 170 may then be inserted and wire 190 placed through the inserted needle, with the needle then being withdrawn. The skin may be incised with a roughly 2 mm incision at the wire insertion site, and a dilator used (optionally at the distal end of insertion sheath 194) to enlarge the tissue track. A distal end 180 of catheter 174 may then be inserted over the needle, with the position of the distal end of the catheter being checked using X-ray or fluoroscopic guidance. The fixation structure near the distal end 180 of catheter 174 may be exposed by proximally withdrawing sheath 182 from over catheter body 176, and the distal end affixed to a target tissue of the heart. Proximal hub 186 of catheter 174 may then be sutured or otherwise affixed to the skin of the patient.

Figure 8F:
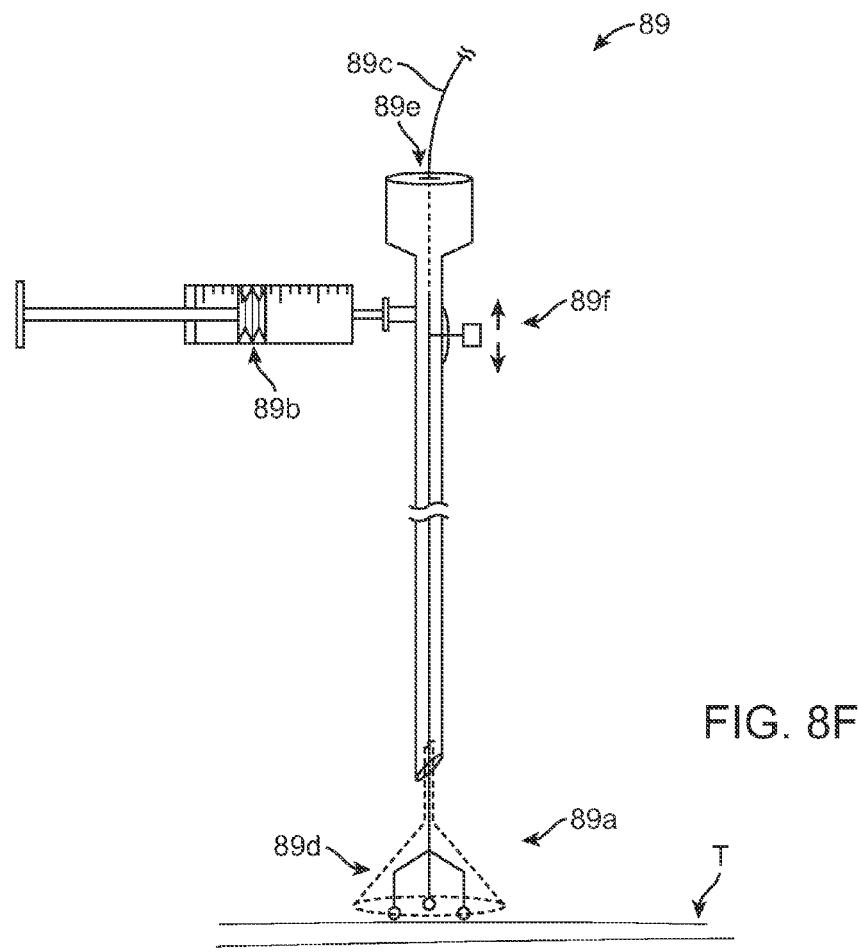

Using fluoroscopic or ultrasound guidance, an alternative affixation approach may comprise deployment of a polyethylene cone from a small profile configuration to a large profile configuration at distal end 180 of catheter 184, as described above regarding FIG. 8F. The cone may be deployed by sliding a switch on the side of the proximal portion of the catheter. A vacuum may be applied to an open end of the cone, optionally using a 10 or 20 cc syringe or the like. A stopcock may be closed to maintain the vacuum, and the syringe removed. Preferably, the cone should affixed via suction to an endocardial surface.

Optionally, a detecting, pacing, or ablating electrode can be placed through a port of catheter hub 186 or through introducer sheath 194. If an active fiducial or surrogate is used, communication between the navigation system and robotic control system may be confirmed.

While the exemplary embodiments have been described in some detail for clarity of understanding and by way of example, a number of changes, modifications, and adaptations may be obvious to those of skill in the art. Hence, the scope of the present invention is limited solely by the appended claims.

What is claimed is:

1. A radiosurgical method for treating a patient body having a target tissue, the target tissue associated with a disease state, the method comprising: acquiring planning image data from the target tissue; planning an ionizing radiation treatment of the target tissue using the planning image data so as to mitigate the disease; implanting a position surrogate within the body by advancing the position surrogate and an elongate flexible body through a blood vessel, releasably coupling the position surrogate to the target tissue so that the position surrogate exhibits movement of the target tissue, detaching the position surrogate from the flexible body and removing the flexible body from the patient body; remodeling the target tissue by directing the planned radiation from outside the body toward the target tissue with reference to the implanted position surrogate thereby mitigating the disease; and monitoring a heartbeat cycle from the body while acquiring the planning image data, and acquiring a time series of three dimensional image data sets distributed throughout the heart beat cycle so as to indicate movement of the target tissue with the heartbeat cycle; wherein the planning of the treatment comprises: identifying radiation sensitive collateral tissue, and determining a series of radiation beams suitable for providing a desired radiation dose in the target tissue without excessively irradiating the collateral tissue; and wherein the remodeling of the target tissue is performed by: monitoring the heartbeat cycle from the body; wherein monitoring the heartbeat cycle from the body comprises obtaining an electrogram of the heart, and tracking at least a portion of the movement of the target tissue in response to the monitored heartbeat cycle while directing the radiation to the target tissue using the time series of datasets.

2. The method of claim 1, wherein the implanting of the surrogate comprises advancing the at least one elongate flexible body through a blood vessel and further comprising determining a time average offset between the surrogate and the target tissue using the time series of image data sets, wherein the tracking of the target tissue is performed by:
   determining a position of the surrogate;
   monitoring the heart beat cycle of the body; and directing the radiation beams to the target tissue using the monitored heart beat cycle, the determined position of the surrogate, and the time average offset.

3. The method of claim 2, wherein the time average offset is determined for the heart cycle by identifying a series of three dimensional offsets from the time series of image data sets, and wherein the time average offset is applied throughout the heart cycle so that tissue deformation between the surrogate and the target tissue during the heart beat cycle is untracked.

4. The method of claim 3, wherein the time average offset is further determined by selecting an image data set from among the time series of image data sets as corresponding to a calculated average of a measured series of offsets so that a selected offset does not necessarily correspond to a quiescent phase of the heart cycle.

5. The method of claim 3, wherein the offset comprises a calculated time average of the identified series of offsets.

6. The method of claim 1, wherein the disease state comprises a disease state of a heart of the patient body.

7. The method of claim 6, wherein the disease state comprises an arrhythmia of the heart.

8. The method of claim 6, wherein the target tissue comprises healthy tissue.

9. The method of claim 1, further comprising explanting the surrogate from the body after remodeling.

10. The method of claim 9, wherein the planning of the treatment further comprises determining an estimated lesion of the target tissue based on the planned ionizing radiation, and reviewing a graphical representation of the estimated lesion.

11. The method of claim 10, wherein the graphical representation of the estimated lesion is reviewed relative to an electrogram of the target tissue.

12. The method of claim 1, wherein the steps of implanting a position surrogate, acquiring planning image data, and planning an ionizing radiation treatment occur prior to a treatment day and wherein the step of remodeling the target tissue occurs on the treatment day.

13. The method of claim 12, wherein the step of implanting a position surrogate occurs prior to the step of acquiring planning image data.

14. The method of claim 12, wherein the surrogate comprises a non-colinear set of discrete fiducial markers so that a three-dimensional offset orientation between the surrogate and the target tissue can be determined from an image of the fiducial markers.

15. The method of claim 12, wherein implanting of the surrogate comprises screwing a helical structure of the elongate body into the target tissue.

16. The method of claim 12, wherein implanting of the surrogate comprises expanding a body within a lumen or cavity adjacent the target tissue.

17. The method of claim 1, further comprising registering the planning image data with the implanted surrogate by acquiring registration data between the implanting of the surrogate and the remodeling of the target tissue, the registration data encompassing the target tissue and the implanted surrogate.

18. The method of claim 17, wherein the registration data comprises three dimensional image data acquired using a first imaging modality, wherein the planning image data is also acquired with the first imaging modality.

19. The method of claim 17, wherein the registration data comprises three dimensional image data acquired using a first imaging modality, wherein the planning image data is acquired using a second imaging modality different than the first image modality.

20. The method of claim 17, wherein the surrogate comprises a plurality of discrete image-able markers implanted so that the markers are sufficiently non-colinear to define a three-dimensional offset orientation.

21. The method of claim 5, further comprising aligning a radiation treatment source with the implanted fiducials by acquiring alignment image data of the surrogate, wherein the target tissue is not sufficiently discernible in the alignment image data for the alignment.

22. The method of claim 1, wherein a location of the target tissue relative to adjacent high-contrast tissue structures of the body moves significantly after the planning image data is acquired and before the target tissue is remodeled.

23. The method of claim 1, further comprising registering a location of the implanted surrogate with the planning image data by implanting one or more image-able fiducial markers of the surrogate at one or more associated target tissue-defined locations, and by identifying the one or more target-tissue defined locations in the planning image data.

* * * * *